(12) United States Patent
Barbarino et al.

(10) Patent No.: US 12,622,505 B2
(45) Date of Patent: May 12, 2026

(54) SYSTEMS, DEVICES, AND METHODS FOR SEGMENT-BASED GUIDANCE OF PRODUCT APPLICATION

(71) Applicant: L'Oreal, Paris (FR)

(72) Inventors: Casey Barbarino, San Anselmo, CA (US); Gregoire Charraud, Jersey City, NJ (US); Juwan Hong, Jersey City, NJ (US)

(73) Assignee: L'Oreal, Paris (FR)

( * ) Notice: Subject to any disclaimer, the term of this patent is extended or adjusted under 35 U.S.C. 154(b) by 324 days.

(21) Appl. No.: 18/345,339

(22) Filed: Jun. 30, 2023

(65) Prior Publication Data

US 2025/0000236 A1     Jan. 2, 2025

(51) Int. Cl.
| | |
|---|---|
| *A45D 44/00* | (2006.01) |
| *A45D 34/04* | (2006.01) |
| *A61B 5/107* | (2006.01) |
| *H04N 1/00* | (2006.01) |

(52) U.S. Cl.
CPC .......... *A45D 44/005* (2013.01); *A45D 34/04* (2013.01); *A61B 5/1077* (2013.01); *H04N 1/00114* (2013.01); *H04N 1/00129* (2013.01); *H04N 1/00251* (2013.01)

(58) Field of Classification Search
CPC ... A45D 44/005; A45D 44/04; H04N 1/00114
See application file for complete search history.

(56) References Cited

U.S. PATENT DOCUMENTS

| | | |
|---|---|---|
| 6,719,565 B1 | 4/2004 | Saita et al. |
| 6,779,686 B2 | 8/2004 | Bartholomew et al. |
| 7,054,668 B2 | 5/2006 | Endo et al. |
| 8,695,610 B2 | 4/2014 | Samain et al. |

(Continued)

FOREIGN PATENT DOCUMENTS

| | | |
|---|---|---|
| CN | 218978266 U | 5/2023 |
| EP | 3673790 A1 | 7/2020 |
| EP | 3 179 880 B1 | 9/2020 |

OTHER PUBLICATIONS

Preliminary Search Report and Written Opinion for FR Pat. App. No. 2309686 filed on Sep. 14, 2023, dated Apr. 1, 2024. 10 pages.

*Primary Examiner* — Ibrahim Siddo
(74) *Attorney, Agent, or Firm* — Christensen O'Connor Johnson Kindness PLLC

(57) ABSTRACT

Devices, systems, and methods for autonomous, semi-autonomous, and assisted manual application of a cosmetic style to a portion of skin of an individual. A printer device includes a printer applicator, a position sensor, and a reservoir for compositions for the cosmetic style. A display of the printer device represents the portion of skin as a plurality of guide segments, and represents the printer applicator as a visual indicator relative to the plurality of guide segments based on the position sensor. The depiction of the visual indicator responds to changes in the position of the printer applicator relative to the portion of the skin to visually guide the individual to accurately apply the cosmetic style, and a feedback device alerts the individual if the application deviates from the portion of the skin. These approaches enable the individual to correct application of the composition in real time.

21 Claims, 16 Drawing Sheets

(56) References Cited

U.S. PATENT DOCUMENTS

| 2006/0098076 | A1 | 5/2006 | Liang | |
| 2020/0167615 | A1* | 5/2020 | Nunokawa | G06K 15/102 |
| 2020/0171831 | A1* | 6/2020 | Lee | B41J 3/407 |
| 2020/0337433 | A1* | 10/2020 | Chung | A45D 34/04 |
| 2023/0066846 | A1 | 3/2023 | Kelley et al. | |

* cited by examiner

*800*

SELECT
A COSMETIC STYLE — *805*

DISPLAY
COSMETIC STYLE ON
IMAGE OF BODY — *810*

TRANSFER COSMETIC
STYLE AS IMAGE FILE
TO PRINTER DEVICE — *815*

MOVE A PRINTER
DEVICE OVER BODY — *820*

PRINT COSMETIC
STYLE ONTO BODY — *825*

SYSTEMS, DEVICES, AND METHODS FOR SEGMENT-BASED GUIDANCE OF PRODUCT APPLICATION

SUMMARY

In an aspect, the disclosure provides a printer device for application of a cosmetic style to a portion of a skin of an individual, the printer device comprising: a printer comprising a printer applicator operably connected to a reservoir comprising a dye therein; a position sensor configured to detect a position of the printer applicator relative to the portion of the skin; a display configured to represent the portion of the skin as a plurality of guide segments, and represent the position of the printer applicator as a visual indicator relative to the plurality of guide segments; wherein a position of the visual indicator as depicted by the display responds to a change in the position of the printer applicator relative to the portion of the skin; and circuitry operably connected to the printer, the position sensor, and the display, wherein the circuitry is configured to: direct the printer to print the cosmetic style with passage of the dye from the reservoir through the printer applicator to the portion of the skin; compute the position of the printer applicator relative to the portion of the skin based on the position sensor; compute a depiction of the visual indicator relative to a guide segment of the plurality of guide segments based on the position of the printer applicator relative to the portion of the skin; and transmit to the display for the depiction of the visual indicator relative to the plurality of guide segments by the display.

In an aspect, the disclosure provides a system for application of a cosmetic style to a portion of a skin of an individual, the system comprising: a printer device; and a smart device comprising circuitry configured to: select the cosmetic style from a plurality of cosmetic styles; display the cosmetic style on an image of the portion of the skin of the individual; and transmit the cosmetic style as a makeup image file to the printer device; wherein the circuitry of the printer device of any other Embodiment is operably connected to the circuitry of the smart device and is further configured to: receive the makeup image file from the smart device; and direct the printer to print the cosmetic style with passage of the dye from the reservoir through the printer applicator to the portion of the skin based on the makeup image file.

In an aspect, the disclosure provides a method of applying a cosmetic style with a printer device, the method comprising: moving the printer device over the portion of the skin of the individual; printing the cosmetic style onto the portion of the skin at a location adjacent to the printer applicator; and guiding movement of the printer device over the portion of the skin based on: the depiction of the visual indicator relative to the plurality of guide segments by the display, and optionally, feedback provided from a feedback device based on a detected deviation of the visual indicator from the guide segment of the plurality of guide segments.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The foregoing aspects and many of the attendant advantages of this invention will become more readily appreciated as the same become better understood by reference to the following detailed description, when taken in conjunction with the accompanying drawings.

DETAILED DESCRIPTION

The disclosure provides devices, systems, and methods for autonomous, semi-autonomous, and assisted manual application of a cosmetic style to a portion of skin of an individual. The disclosed approaches enable the individual to correct application of the composition in real time for more accurate placement of the cosmetic style to the portion of skin. Printer devices are useful alone or in combination with smart devices, such as smartphones, for planning, selection, and implementation of cosmetic styles among a plurality of cosmetic styles.

Figure 1A:
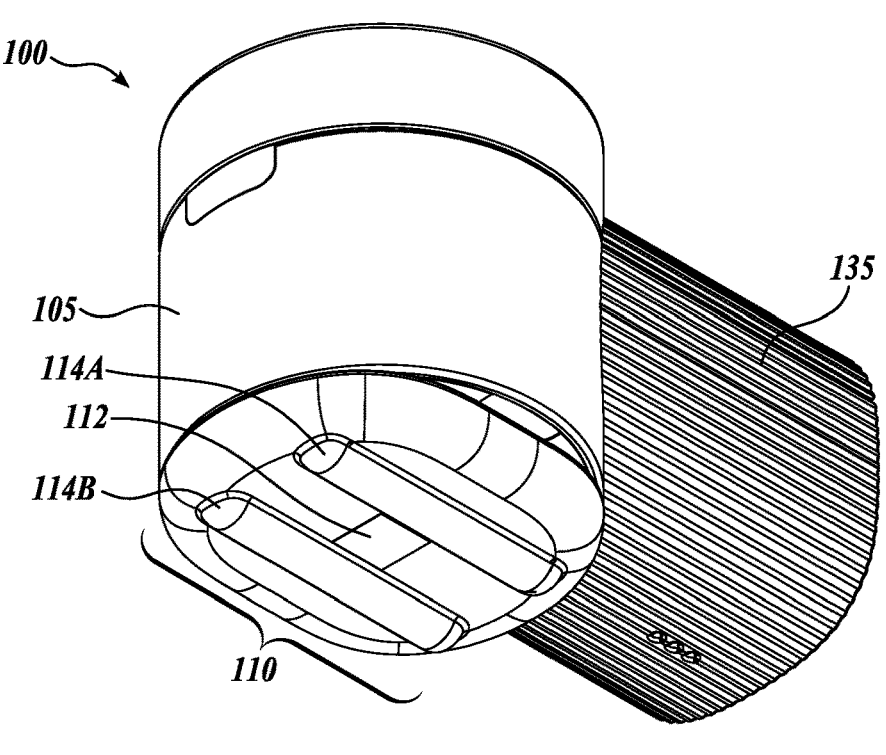
FIG. 1A shows a lower front side perspective view of an example printer device for application of a cosmetic style to a portion of a skin of an individual.
Figure 1B:
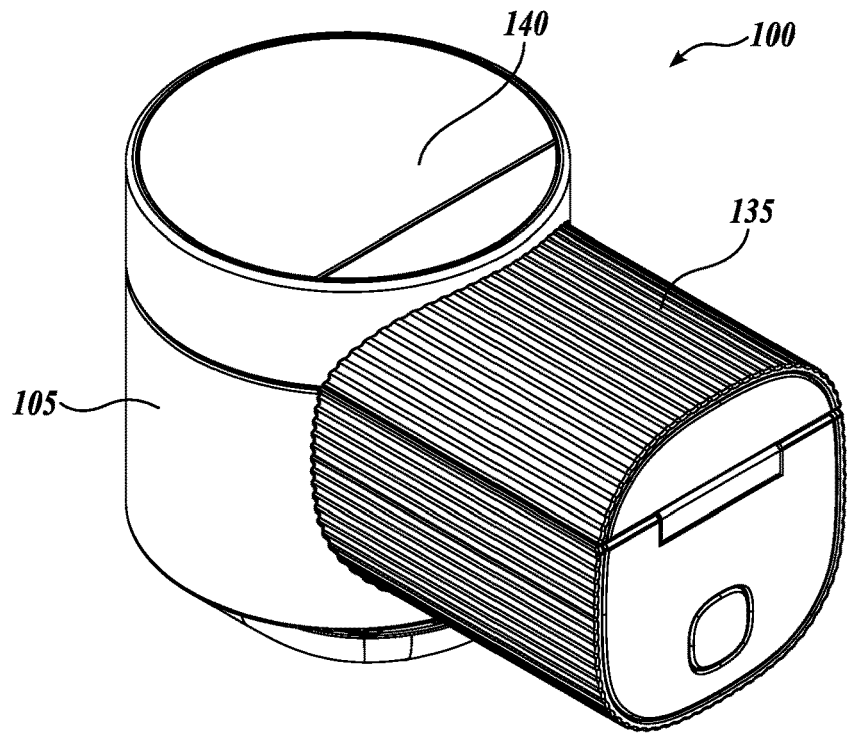
FIG. 1B shows an upper rear side perspective view of the example printer device.

As shown at FIG. 1A and FIG. 1B, a printer device 100 includes a printer applicator 112, a position sensor, and a reservoir for compositions for the cosmetic style. A display 140 of the printer device 100 represents the portion of skin as a plurality of guide segments, and represents the printer applicator as a visual indicator relative to the plurality of guide segments based on the position sensor. The depiction of the visual indicator responds to changes in the position of the printer applicator relative to the portion of the skin to visually guide the individual to accurately apply the cosmetic style, and a feedback device or component alerts the individual if the application of the cosmetic style deviates or starts to deviate from the portion of the skin to enable the individual to correct the course of the application.

A printer device 100 is configured for application of a cosmetic style to a portion of a skin of an individual, and comprises a printer 110, a position sensor, a display 140, and circuitry for carrying out all or part of an operation or method of the disclosure. The printer 110 comprises a printer applicator 112 operably connected to a reservoir (145 of FIG. 2A) comprising a dye therein, and the position sensor is configured to detect a position of the printer applicator 112 relative to the portion of the skin. The display 140 is configured to represent the portion of the skin as a plurality of guide segments (155 of FIG. 5A), and represent the position of the printer applicator as a visual indicator (e.g., an arrow, a circle, a square, a triangle, and the like) relative to the plurality of guide segments. A position of the visual indicator as depicted by the display 140 responds to a change in the position of the printer applicator 112 relative to the portion of the skin, as a result of the position sensor.

Circuitry of printer device 100, which includes but is not limited to a processor, a microprocessor, processor circuitry, and/or dedicated hardware circuitry, operably connects the printer 110, the position sensor, and the display 140. The circuitry is configured to direct the printer 110 to print the cosmetic style with passage of the dye from the reservoir through the printer applicator 112 to the portion of the skin, compute the position of the printer applicator 112 relative to the portion of the skin based on the position sensor, compute a depiction of the visual indicator relative to a guide segment of the plurality of guide segments based on the position of the printer applicator relative to the portion of the skin, and transmit to the display 140 for the depiction of the visual indicator relative to the plurality of guide segments by the display 140. In embodiments, circuitry of printer device 100 is configurable with a processor and processor-executable instructions stored on a non-transitory machine-readable medium of printer device 100, as a non-limiting example, but other approaches for configuring circuitry of printer device 100 can be implemented in embodiments.

As shown at FIGS. 1A and 1B, in embodiments, printer device 100 includes a housing 105 and a handle 135. Printer device 100 is shown with a cylindrical housing 105 and a cylindrical handle 135, but can be implemented according to any number of shapes and form factors. In embodiments, printer device 100 does not have handle 135 as shown. In embodiments, printer device 100 includes internal circuitry, including a processor, a power source, such as a battery, and the like, for electronic operation of printer device 100.

In embodiments, printer device 100 includes a processor for execution of instructions stored on a non-transitory machine-readable medium, for enabling the processor to carry out all or part of a method or process of the disclosure. In embodiments, the processor is configured to receive a makeup image file, detect a position and a curvature of a portion of skin of an individual based on the position sensor, and direct printer 110 to print a cosmetic style based on the makeup image file at a location on the portion of skin. In embodiments, the location is determined by a cosmetic style. For example, a lipstick cosmetic style can be printed on the lips of the individual, a brow makeup can be printed to the eyebrow of the individual, and the like.

In embodiments, printer device 100 is powered through a wired connection, e.g., a wired electrical connection with a source of alternating current; however, in embodiments, printer device 100 is independently powered, such as with a battery or a capacitor. In embodiments, printer device 100 includes a charging port configured to receive electricity from a power source to recharge a battery or capacitor of the printer device 100.

In embodiments, housing 105 houses printer 110. In embodiments, printer 110 is positioned on a first side of the printer device 100, and display 140 is positioned on a second side of the printer device 100, as shown at FIGS. 1A and 1B. In embodiments, printer 110 includes a printer applicator 112 and one or more spacers 114A and 114B.

Figure 2A:
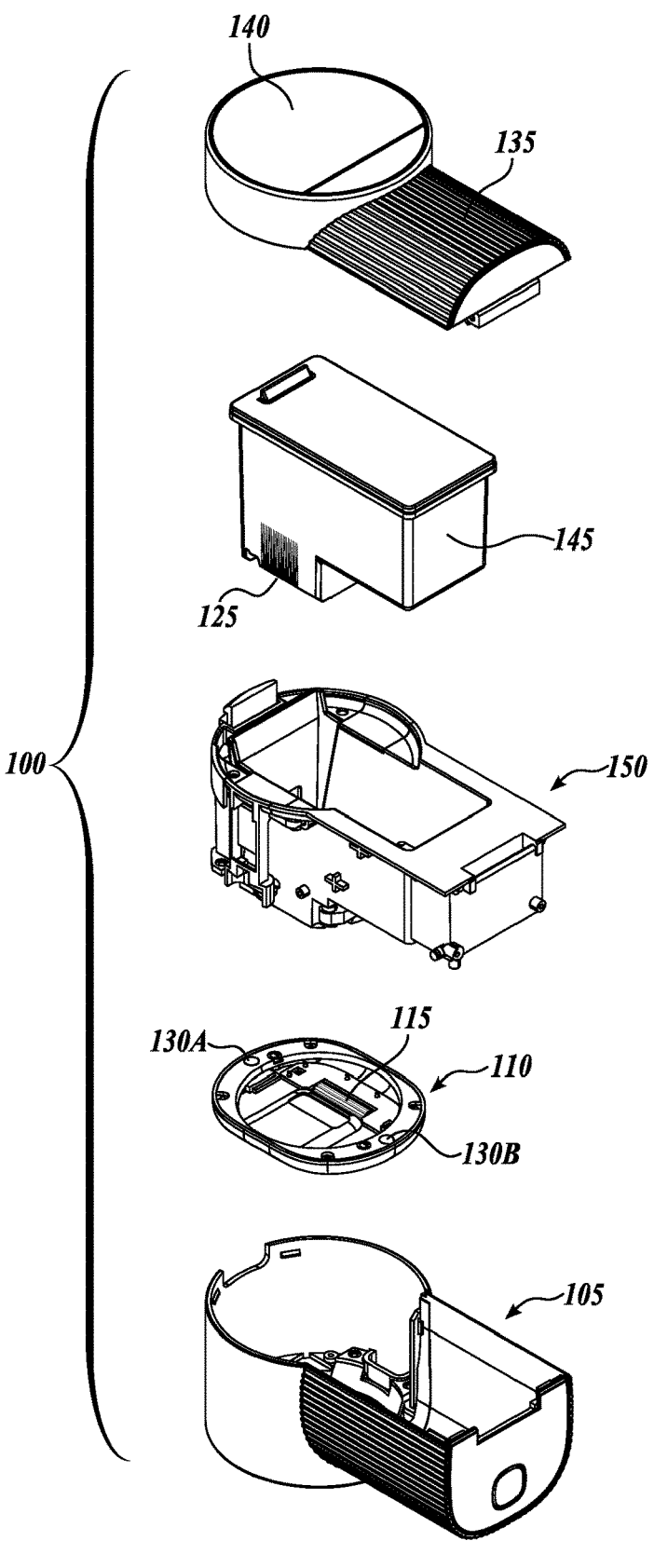
FIG. 2A shows an upper exploded view of the example printer device.
Figure 2B:
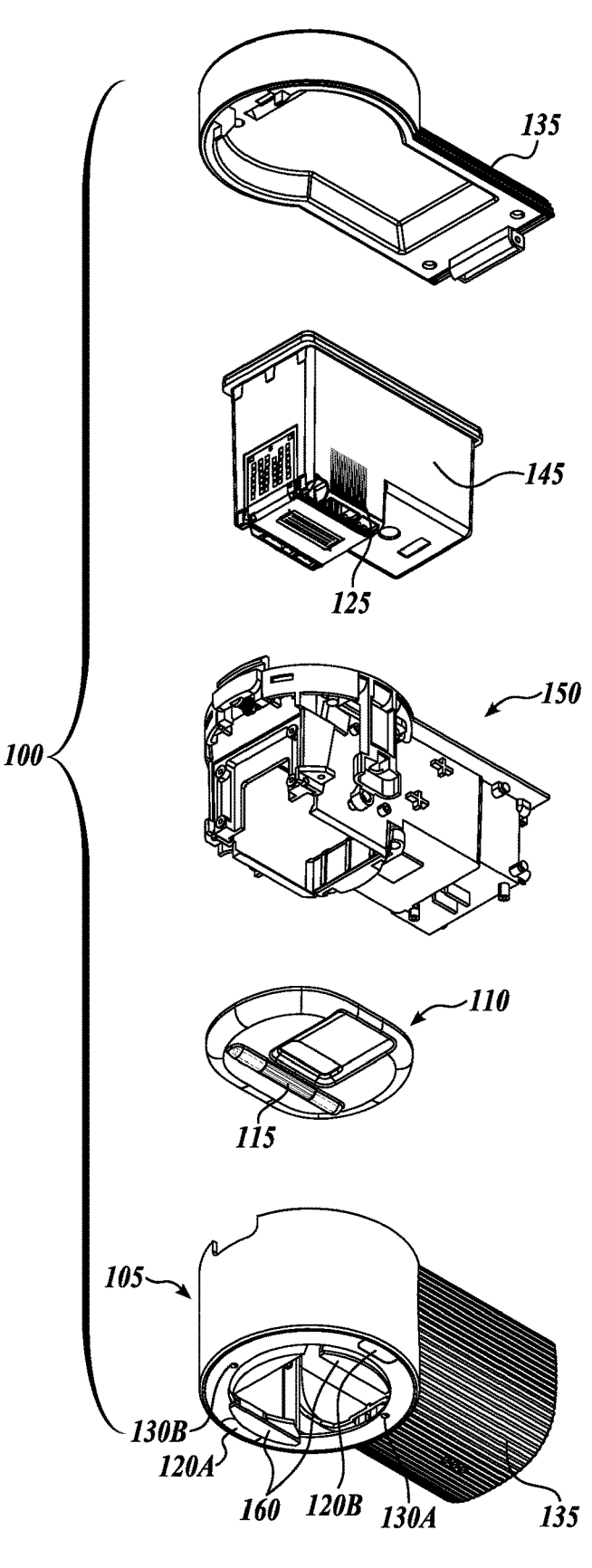
FIG. 2B shows a lower exploded view of the example printer device.

In embodiments, printer applicator 112 is configured to facilitate printer 110, as shown at FIG. 2B, to print a cosmetic style onto a surface. In embodiments, printer applicator 112 is rectangular, square, circular, organically shaped, or the like. In embodiments, printer applicator 112 is in the middle of a front side of housing 105. In embodiments, printer applicator 112 is between spacers 114A, 114B.

While two spacers 114A and 114B are illustrated, it should be understood that any number and configuration of spacers 114A. 114B can be positioned on printer 110. In embodiments, spacers 114A, 114B are rounded polygons, as shown at FIG. 1A, but it should be understood that spacers 114A, 114B can be implemented as any number of forms including spherical, rectangular, and organically shaped. In embodiments, spacers 114A, 114B are configured to contact a surface while printer device 100 is passed over it, such that an optimal distance between printer 110 (or printer applicator 112) and the surface is maintained. In embodiments, spacers 114A, 114B have a thickness that enables printer applicator 112 to be in contact with a curved surface. In embodiments, spacers 114A, 114B are configured to roll. In embodiments, spacers 114A, 114B include at least one position sensor, as described herein. In embodiments, in addition to maintaining a distance between printer applicator 112 and the surface, spacers 114A, 114B are configured to roll on the surface as printer device 110 prints the cosmetic style to the surface.

In embodiments, printer device 100 includes a position sensor operably coupled to printer 110, as shown at FIG. 2A. In embodiments, position sensor is housed inside housing 105, but in at least some embodiments, position sensor is located on the front side of printer device 100 with printer applicator 112. In embodiments, the position sensor is positioned inside one or both spacers 114A, 114B. In embodiments, printer device 100 further includes a camera, as shown at FIG. 2A. In embodiments, the camera is configured to capture a plurality of images as printer 110 moves over a portion of skin, such as a facial feature of an individual. In embodiments, the facial feature is an eyebrow, a nose, an eye, a wrinkle, acne, or the like.

In embodiments, printer 110 is a rotatably adjustable body printer 110. In embodiments, printer 110 is configured to articulate to scan a surface more accurately, such as a body, skin, or hair. In such embodiments, position sensor 115 can be a sensor wheel as described herein. In operation, position sensor 115 contacts the surface and rolls as the printer 110 scans the surface. In such embodiments, printer device 100 is able to consider the curvature of the surface, which can be a portion of a human body. In embodiments, printer 110 is adjustable to fit the needs of different body types and printing environments. In embodiments, printer 110 has an adjustable printer applicator 112. In embodiments, spacers 114A, 114B are movable or adjustable to change the size of printer applicator 112. In embodiments, printer applicator 112 is concave or convex to better contact the surface. In embodiments, printer 110 configured for being articulated, so as to better contact the surface. In embodiments, printer 110 is coupled to printer device 100 with a flexible connector, as shown at FIG. 2B. In embodiments, the flexible connector is a pivot, a hinge, or a joint. In embodiments, the flexible connector allows printer 110 to be articulated. In embodiments, this allows for more accurate scans of a surface. In embodiments, this further allows the printer 110 to determine a curvature of a surface.

In embodiments, printer device 100 includes a display 140, configured for use as a user interface. Though display 140 is shown on the back side of printer device 100, in embodiments, display 140 is a separate component, such as a smartphone or tablet. In embodiments, display 140 is round, but in other embodiments, can be implemented in any form, such as rectangular or oblong. In embodiments, display 140 includes one or more actuators, such as buttons or keys. In embodiments, display 140 includes a touch type capacitance button. In embodiments, display 140 is a touchscreen. In embodiments, the display includes one or more output modules configured to output an alert, such as feedback, to the user. In embodiments, the alert is a sound, vibration, or the like. In embodiments, the alert includes an indication as to how or in what direction to move printer device 100 during use.

FIG. 2A shows an upper exploded view, and FIG. 2B shows a lower exploded view, of the example printer device. In embodiments, printer device 100 includes an internal component 150, printer 110, and position sensor 115. In embodiments, printer device 100 includes a reservoir 145 and a processor 125. In embodiments, internal component 150 is configured to hold printer 110 in place within housing 105. In embodiments, internal component 150 is structurally coupled to printer 110 and reservoir 145.

In embodiments, printer 110 includes position sensor 115 and one or more cameras 120A, 120B. In embodiments, cameras 120A, 120B are located on printer 110 but in at least some embodiments, cameras 120A, 120B are located on housing 105. In embodiments, as printer 110 moves across a surface, such as an individual's face, cameras 120A, 120B capture a plurality of images of the surface. In embodiments, cameras 120A, 120B capture a plurality of images of a facial feature as the printer device 100 moves over the facial feature. In embodiments, printer device 100 includes two cameras 120A and 120B. In embodiments, such as illustrated at FIG. 2B, a first camera 120A is located at a first portion of the printer device 100, and a second camera 120B is located at a second portion of the printer device 100, e.g., opposite the first portion.

In embodiments, as shown at FIG. 2B, printer device 100 includes one or more light sources 130A, 130B. In embodiments, light sources 130A, 130B are LEDs. Though two light sources 130A, 130B are shown, any number of light sources can be implemented on the printer device 100, according to embodiments. In embodiments, light sources 130A, 130B are positioned on the printer 110, but in other embodiments, light sources 130A, 130B are positioned on the front side of printer device 100.

In embodiments, printer 110 includes one or more position sensors 115. While one position sensor 115 is shown at FIG. 2A, it should be understood that any number of position sensors 115 can be implemented. In embodiments, at least one position sensor 115 is a rolling position sensor 115, such as a sensor wheel. In such embodiments, position sensor 115 is configured to roll across the facial feature as printer 110 is moved over the facial feature. In this manner, position sensor 115 detects a position of the facial feature as the printer device 100 moves over the facial feature. In embodiments, position sensor 115 is further configured to detect the curvature of the facial feature or the user's face, i.e., the portion of the skin of the individual.

In embodiments, printer device 100 includes a processor 125. In embodiments, processor 125 is operably and/or communicatively coupled to printer 110, position sensor 115, and camera 120. The processor 125 is configurable to receive a makeup image file, detect a position and a curvature of the portion of the skin based on the position sensor, and direct the printer to print the cosmetic style based on the makeup file at a location. In embodiments, processor 125 is further configured to detect the lighting of the facial feature, and direct one or more light sources 130A, 130B to illuminate the facial feature. While one processor 125 is illustrated, it should be understood that any number of processors can be implemented into printer device 100.

In embodiments, printer device 100 includes a reservoir 145. In embodiments, the reservoir 145 is configured to hold one or more cosmetic inks or dyes, or other compositions for the cosmetic style. In embodiments, the reservoir holds any number of cosmetic inks or dyes as needed to print the cosmetic style. In embodiments, the reservoir 145 includes one or more cartridges, such that reservoir 145 can hold any number of colors, compositions, finishes, or formulations of the cosmetic inks or dyes.

In embodiments, processor 125 is further communicatively coupled to reservoir 145 and printer 110. In embodiments, processor 125 directs reservoir 145 and printer 110 to fabricate a cosmetic style, such as a temporary tattoo, or makeup printed in the shape of the facial feature. In embodiments, the cosmetic style is selected from an eyebrow, an eyeshadow, a concealer, a primer, a foundation, a blush, a lipliner, a lipstick, a bronzer, an eyeliner, a freckle pattern, a facial hair, a hair design, such as facial hair or a hairline design, or a highlighter.

In embodiments, printer 110 is coupled to the printer device 100 with a flexible connector 160. In embodiments, flexible connector 160 is a pivot, a hinge, or a joint. In embodiments, flexible connector 160 enables printer 110 to be articulated. In embodiments, this allows for more accurate scans or printing of the surface. In embodiments, this further allows printer 110 to determine a curvature of the surface.

Figure 3:
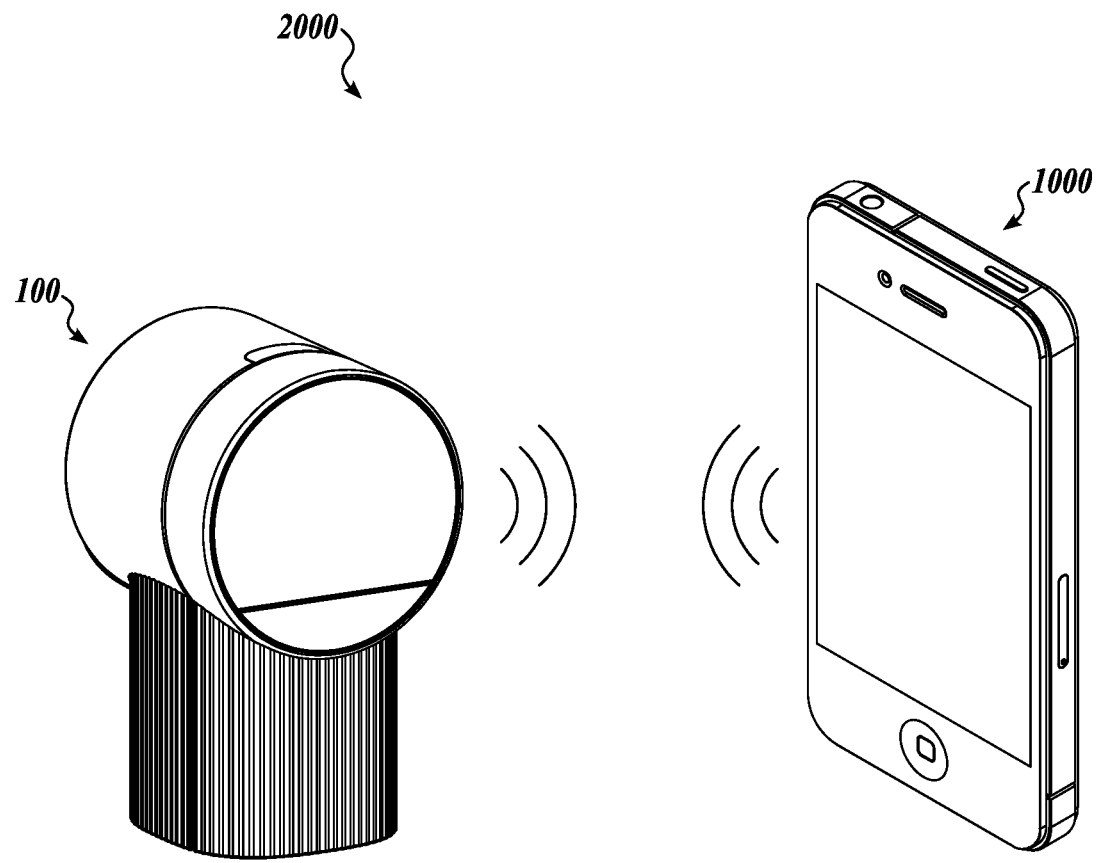
FIG. 3 shows a first example system for application of a cosmetic style to a portion of a skin of an individual.
Figure 4:
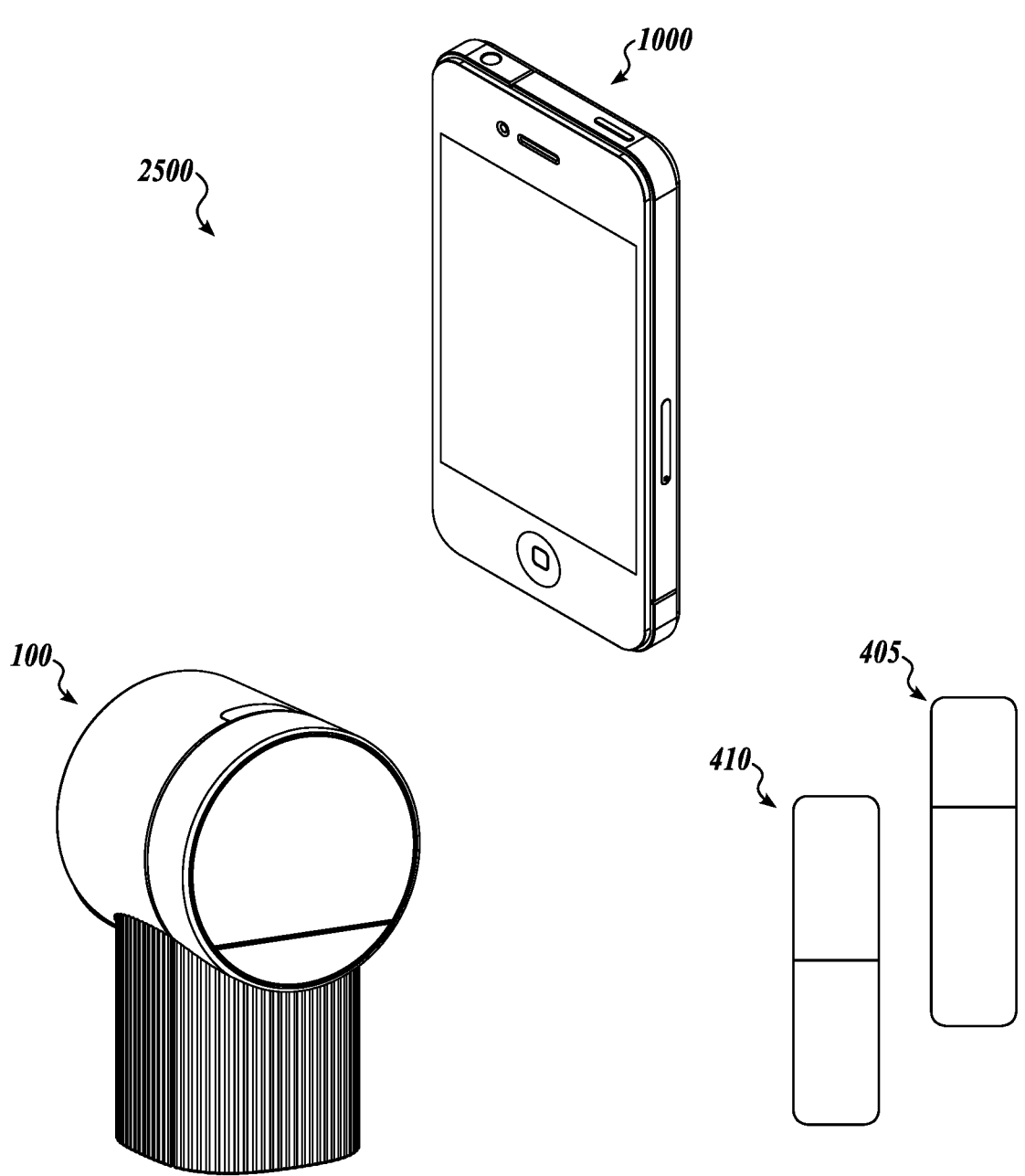
FIG. 4 shows a second example system for application of a cosmetic style to a portion of a skin of an individual.

FIG. 3 shows a first example system 2000 for applying a cosmetic style, in accordance with the disclosure. System 2000 for applying a cosmetic style includes a smart device 1000 and a printer device 100. The system 2000 of FIG. 3, and system 2500 of FIG. 4, is generally configured for application of a cosmetic style to a portion of a skin of an individual. The system comprises a printer device 100 and a smart device 100 that comprises circuitry configured to select the cosmetic style from a plurality of cosmetic styles, display the cosmetic style on an image of the portion of the skin of the individual, and transmit the cosmetic style as a makeup image file to the printer device. The circuitry of the printer device 100 is operably connected (or is operably connectable) to the circuitry of the smart device 1000 and is further configured to receive the makeup image file from the smart device 1000 and direct the printer to print the cosmetic style with passage of the dye from the reservoir through the printer applicator to the portion of the skin based on the makeup image file. In example embodiments, the smart device 1000 is a smartphone or other consumer computational device and the circuitry of the smart device 1000 is configurable with a processor or microprocessor programmable with processor-executable instructions stored on a non-transitory machine-readable medium of the smart device 1000.

Accordingly, in embodiments, smart device 1000 includes a software application configured to select a cosmetic style from a plurality of cosmetic styles, display the cosmetic style on an image of a portion of skin of the individual, and transmit the cosmetic style as a makeup image file, as shown and described herein in detail at FIGS. 6A, 6B, and 7A-7D. In embodiments, as illustrated at FIG. 3, smart device 1000 is a smartphone. It should be understood that smart device 1000 can be implemented according to any number of forms, including but not limited to a tablet, laptop, or computer. In embodiments, smart device 1000 is operably and/or communicatively coupled to printer device 100. In embodiments, smart device 1000 is communicatively coupled to printer device 100 by a wireless connection, such as a Bluetooth® connection, a Bluetooth® low energy (BLE) connection, and/or a Wi-Fi® connection, and/or a wired connection.

In embodiments, printer device 100 includes a position sensor, a reservoir configured to hold one or more compositions, and a printer including a printer applicator. In embodiments, the printer is configured to print the cosmetic style with passage the composition through the printer applicator. In embodiments, printer device 100 further includes a processor configured to receive the makeup image file, detect a position and a curvature of the portion of skin based on the position sensor, and direct the printer to print the cosmetic style, e.g., at a specific location, as described herein.

FIG. 4 shows a second example system 2500 for autonomously applying a cosmetic style, in accordance with the disclosure. In embodiments, system 2500 further includes a primer 405, and a topcoat 410. In embodiments, primer 405 is configured to be applied before the cosmetic style. In embodiments, primer 405 is held in a container, such as shown at FIG. 4. In embodiments, primer 405 includes an applicator configured to brush on, spread, or apply primer 405. In embodiments, primer 405 is added to a surface manually, such as with the hand of a user of system 2500. In embodiments, primer 405 is configured to prime the surface of an individual's skin or hair to accept the cosmetic style. In embodiments, primer 405 has an adhesive property, such that it sticks to the cosmetic style. In embodiments, primer 405 is placed inside a reservoir of printer device 100. In embodiments, primer 405 is printed by the printer device 100. Primer 405 may be implemented according to any form, such as a solid, a liquid, a cream, or a gel. In embodiments, primer 405 is configured to be sprayed onto the surface.

In embodiments, system 2500 further includes a topcoat 410 configured to be applied after the cosmetic style. In embodiments, topcoat 410 is held in a container, such as shown at FIG. 4. In embodiments, topcoat 410 includes an applicator configured to brush on, spread, or apply topcoat 410. In embodiments, topcoat 410 is added to a surface manually, such as with the hand of a user of system 2500. In embodiments, topcoat 410 seals the cosmetic style to keep the cosmetic style from smudging, smearing, moving, fading, or otherwise be damaged or degraded. In embodiments, topcoat 410 has an aesthetic property, such as a finish. In embodiments, the finish may be a glitter finish, a glossy finish, a dewy finish, a matte finish, or the like. In embodiments, topcoat 410 is placed inside a reservoir of printer device 100. In embodiments, topcoat 410 is printed by printer device 100. Topcoat 410 may be implemented according to any form, such as a solid, a liquid, a cream, or a gel. In embodiments, topcoat 410 is configured to be sprayed onto the surface.

Figure 5A:
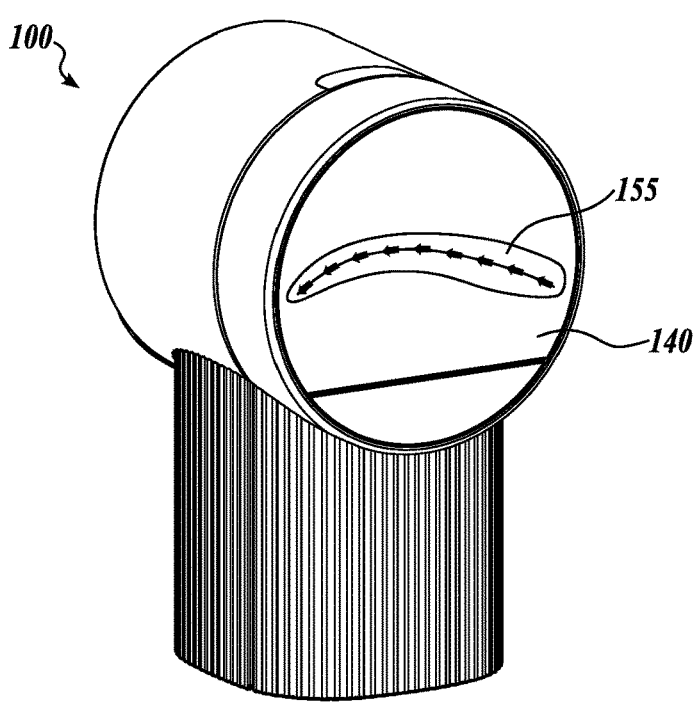
FIG. 5A shows a rear perspective view of the example printer device with a plurality of guide segments thereon.
Figure 5B:
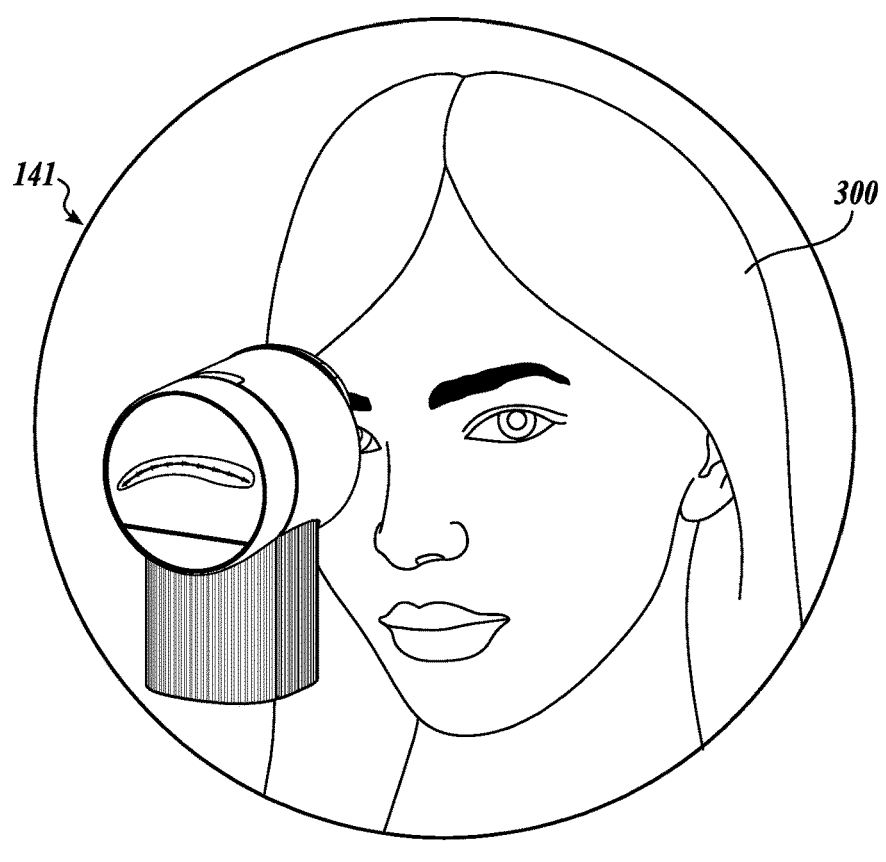
FIG. 5B shows a rear perspective view of the example printer device with the plurality of guide segments thereon, during use to apply a cosmetic style to an eyebrow of an individual.

FIGS. 5A-5B show an example display 140 of an example printer device 100, in accordance with the disclosure, showing a plurality of segmented guidelines 155 for guiding movement of the printing device when applying 141 the cosmetic style to the portion of skin of the individual 300. In embodiments, display 140 depicts a printing guide, as a plurality of segmented guidelines 155, to guide a user to properly use the printer device 100. In embodiments, display 140 shows one or more of the plurality of images as described herein of a facial feature or surface and an arrow pointing in a direction a user can move the printer device. In embodiments, the plurality of segmented guidelines 155 includes a graphical representation of the facial feature and an arrow pointing in the direction a user can move the printer device along the plurality of segmented guidelines 155.

In embodiments, display 140 depicts a current or live view of a camera of printer device 100. In embodiments, as the individual moves the printer device 100 over the surface, an image captured by the camera is displayed on display 140. In embodiments, the printer device 100 includes a feedback device or component for one or more alerts to direct the user to move or correct movement of the printer device. In embodiments, the alerts are visual alerts, such as arrows, or auditory alerts, such as chimes or alarms, or tactile alerts such as vibrations or haptic feedback.

Figure 6B:
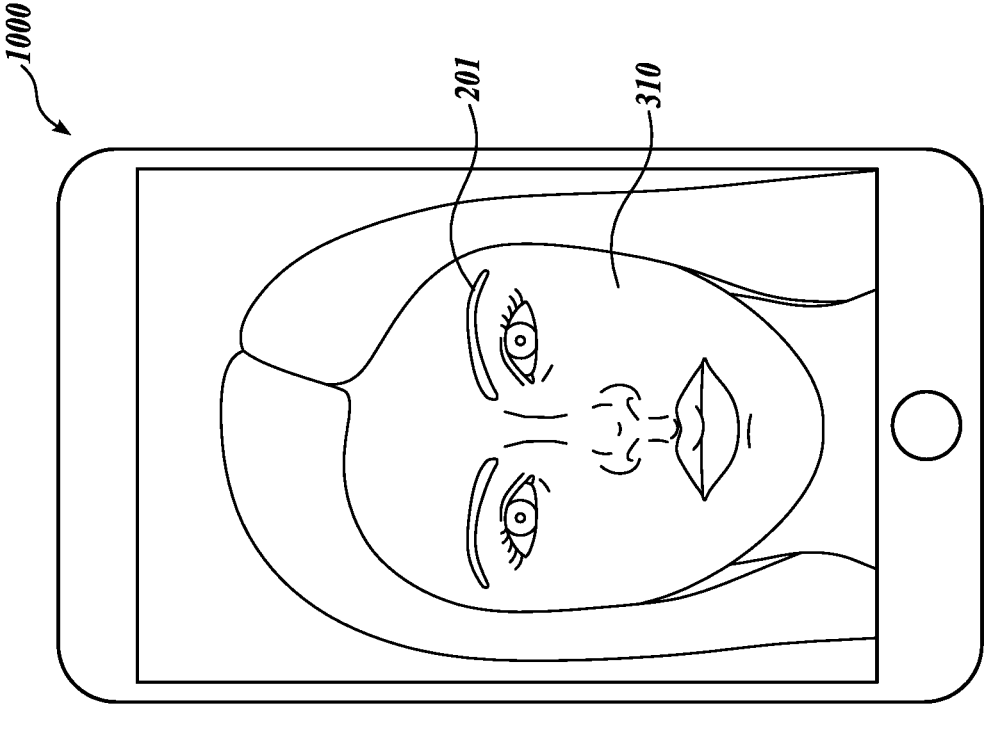
FIG. 6B shows an example image of an individual for planning, depiction, or selection of a cosmetic style from a plurality of cosmetic styles.
Figure 6B:
Figure 6A:
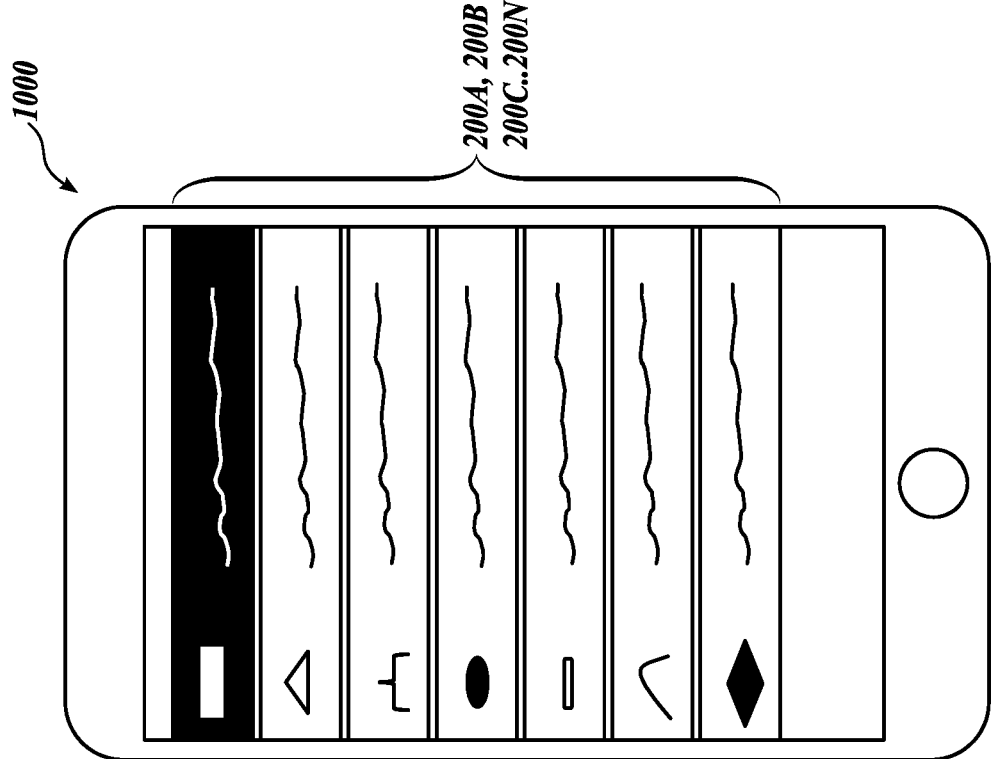
FIG. 6A shows an example user interface of a smart device of a system for depiction or selection of a cosmetic style from a plurality of cosmetic styles.

FIGS. 6A-6B show example processes of an example system during use, in accordance with the disclosure. In embodiments, the system comprises system 2000, system 2500, or another system as described herein. FIG. 6A shows a user interface of an example software application of a smart device 1000. In embodiments, the software application depicts a plurality of cosmetic styles 200A, 200B, 200C . . . 200N. In embodiments, a user selects a cosmetic style of the plurality of cosmetic styles 200A, 200B, 200C . . . 200N. In embodiments, the user selects the cosmetic style by clicking, tapping, or otherwise choosing the cosmetic style. In FIG. 6A, a selected cosmetic style is shown in black (i.e., top row). In embodiments, the software application displays the plurality of cosmetic styles 200A, 200B, 200C . . . 200N as a list or drop-down menu. In embodiments, each cosmetic style of the plurality of cosmetic styles 200A, 200B, 200C . . . 200N includes a graphical representation of the cosmetic style, a description of the cosmetic style, or both. In embodiments, the software application is further configured to recommend a cosmetic style from the plurality of cosmetic styles 200A, 200B, 200C . . . 200N to the user. In embodiments, the recommendation is based on a trending cosmetic style, a color of the user's hair, skin, or lips, a past cosmetic style selected by the user, a shape of the user's eyes, eyebrows, nose, lips, checks, or forehead, a location of the user, or a color of the user's clothing, or another feature or characteristic of the user or other individual.

FIG. 6B shows an example graphic of a software application on the smart device 1000, displaying an overlay of the selected cosmetic style 201 on an image of the user's face 310. In embodiments, the image is a live video feed from a camera of the smart device 1000 or a camera of the printer device (not shown at FIG. 6B). In embodiments, the image is a static photo, or a previously taken video. In such embodiments, the user uploads a photo or a video to the smart device 1000 where it is shown by the software application.

Figure 7B:
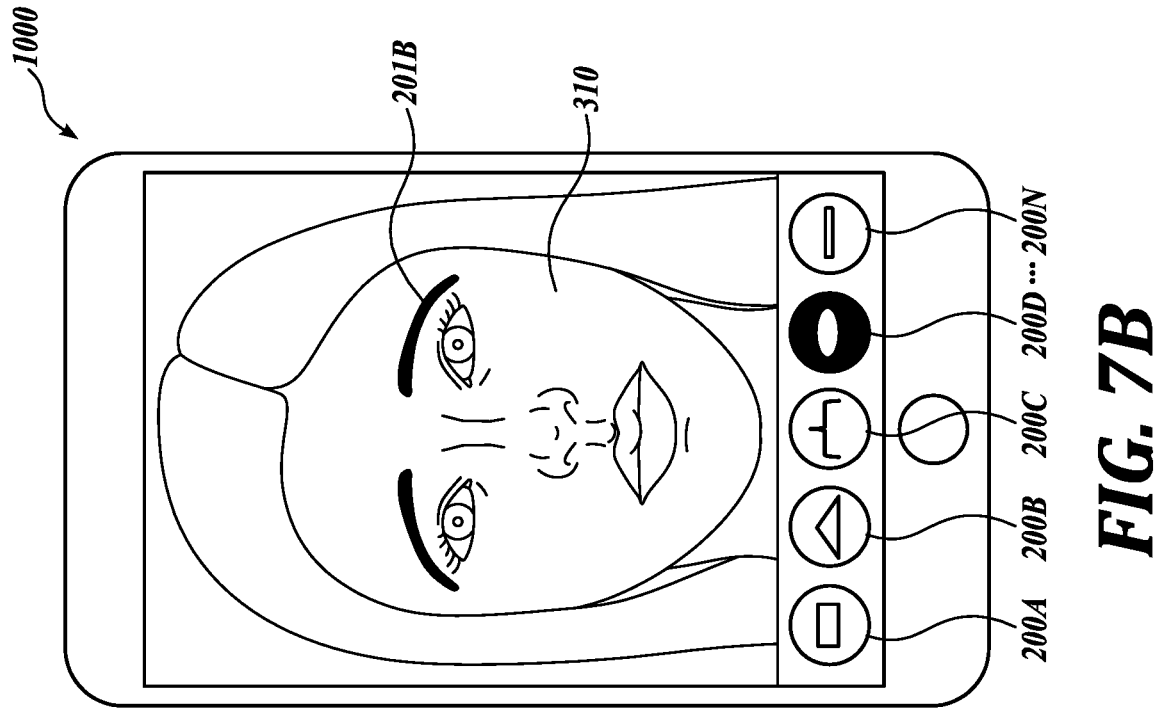
FIG. 7B shows an example overlay image of a second cosmetic style virtually applied to a portion of skin of the individual.
Figure 7A:
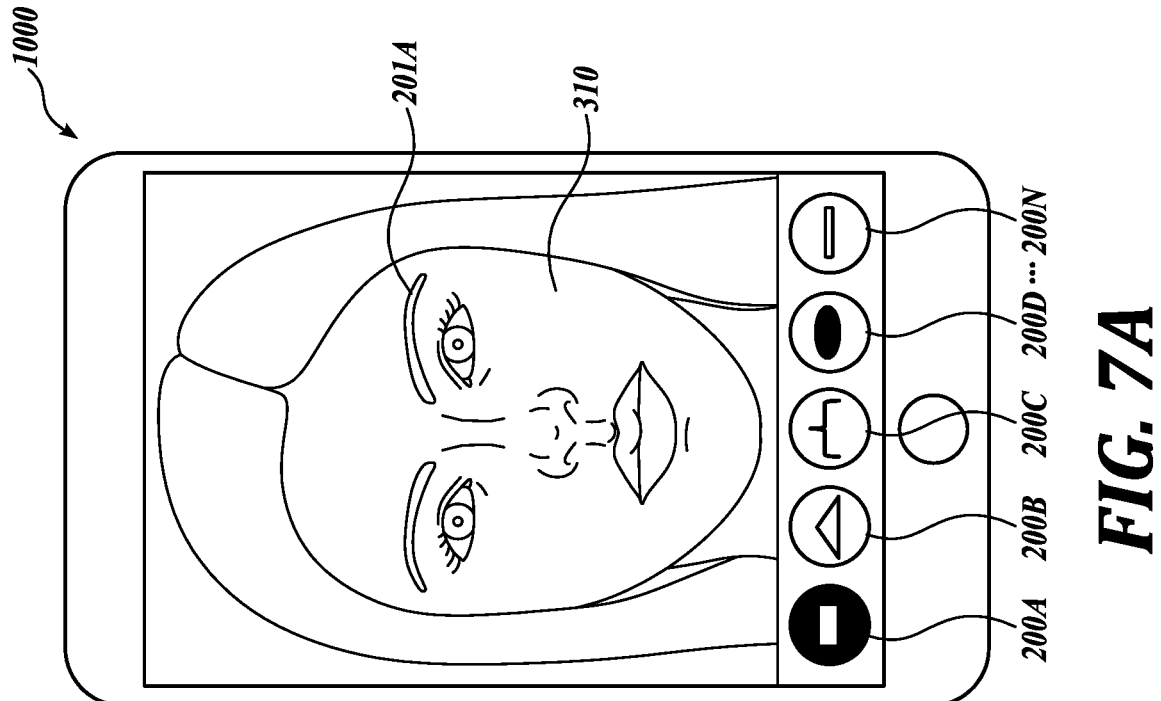
FIG. 7A shows an example overlay image of a first cosmetic style virtually applied to a portion of skin of the individual.

FIGS. 7A-7D show example processes of an example system in use, in accordance with the disclosure. In embodiments, the system is system 2000, system 2500, or another system as described herein. FIG. 7A shows an example software application of a smart device 1000. In embodiments, FIG. 7A follows FIG. 6B in a sequence of steps. In embodiments, a user scrolls through a plurality of cosmetic styles 200A, 200B, 200C. 200D . . . 200N while the smart device displays an image of the user's face 310 and the selected cosmetic style 201A. In such embodiments, the user selects a cosmetic style 210A and change selections among cosmetic styles of the plurality of cosmetic styles 200A. 200B, 200C, 200D . . . 200N in real time. In embodiments, the plurality of cosmetic styles 200A, 200B, 200C, 200D . . . 200N are shown by the smart device 1000 in such a manner that depiction of the styles does not obscure the image of the user's face 310, such as at a bottom, top, or side of a screen of the smart device 1000. As shown at FIG. 7A, cosmetic style 200A is selected and is displayed as an overlay on the user's face as selected cosmetic style 201A. As shown at FIG. 7B, the user has selected a new cosmetic style 200D, which is displayed as an overlay on the image of the user's face 310 as selected cosmetic style 201B. In this manner, the user can change selections between any number of cosmetic styles from the plurality of cosmetic styles 200A, 200B, 200C, 200D . . . 200N before adjusting or printing a cosmetic style.

Figures 7C, 7D:
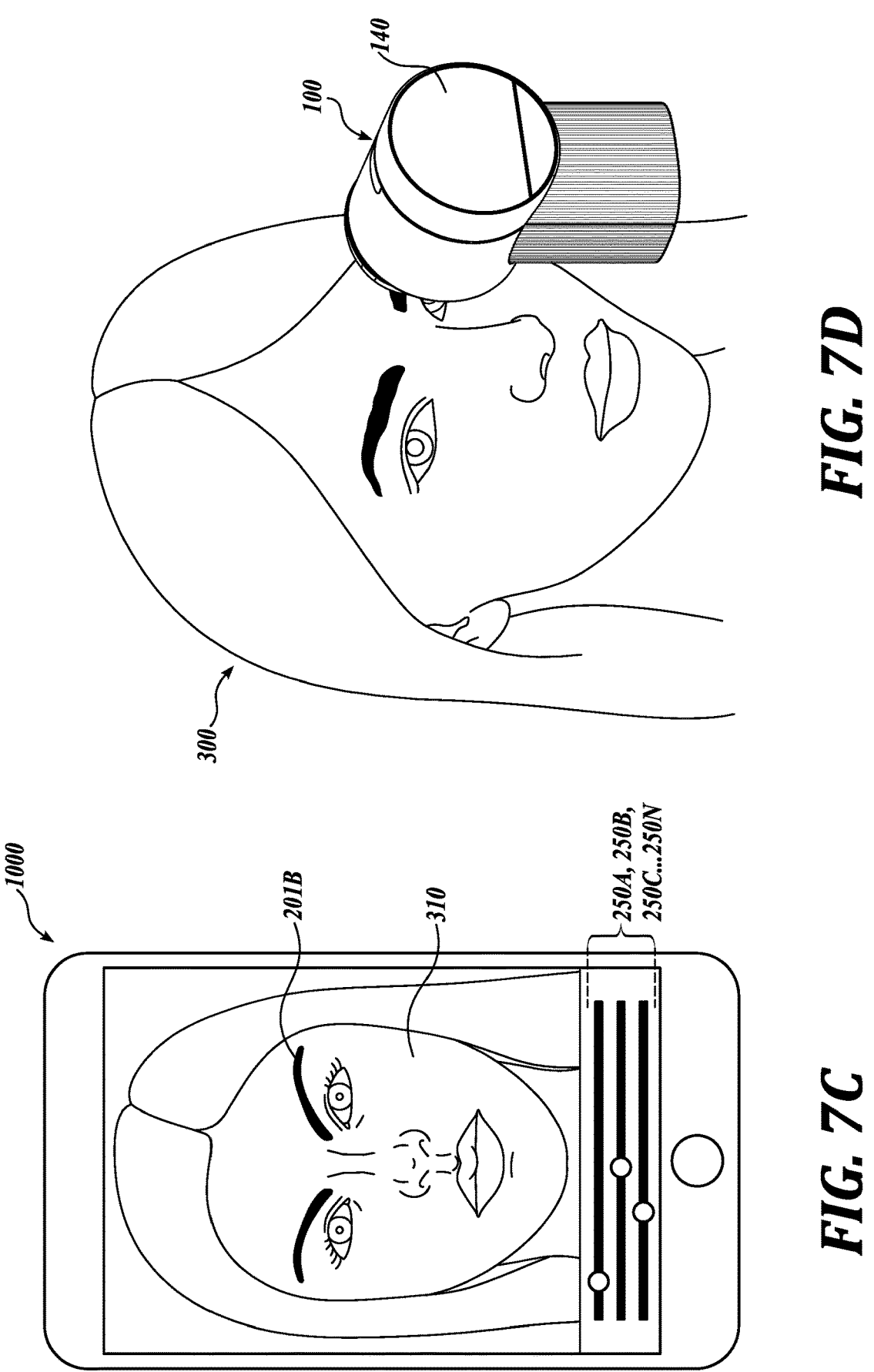
FIG. 7C shows an example overlay image of a third cosmetic style virtually applied to a portion of skin of the individual.
FIG. 7D shows a perspective view of an example printer device in use to apply a cosmetic style to a portion of skin of an individual.

FIG. 7C shows a user adjusting the selected cosmetic style 201B to fit their preferences. In embodiments, FIG. 7C follows FIG. 6B in a sequence of steps. In embodiments, the application suggests adjustments to the selected cosmetic style 201B. In embodiments, the suggested adjustments are based on a shape of the user's face, the shape of a facial feature of the user, a color of the user's hair, skin, eyes, or clothing, or a trending adjustment, e.g., an adjustment that is trending with one or a plurality of users. In embodiments, adjusting the selected cosmetic style 201B includes changing a color, a size, a length, a width, a hair size, a pattern, an angle, a position, a location of the cosmetic style, or a combination thereof of the cosmetic style 201B. In embodiments, such as when the cosmetic style 201B includes discrete elements, the discrete elements of the cosmetic style 201B can be adjusted independently. For example, if the selected cosmetic style 201B is a makeup overlay of a pair of eyebrows (as shown at FIG. 7C) each eyebrow of cosmetic style 201B can be adjusted independently. As another example, if the cosmetic style 201B is a lipstick, a blush, and an eyeshadow, the lipstick, the blush, and the eyeshadow can all be adjusted independent of one another.

In embodiments, the selected cosmetic style 201B is adjusted with a plurality of sliders 250A, 250B, 250C . . . 250N. In embodiments, the selected cosmetic style 201B is adjusted with another mechanism, such as a plurality of presets, manipulation of the selected cosmetic style 201B with a touch screen, or otherwise. Once the user is satisfied with the selected cosmetic style 201B, the user can transmit the selected cosmetic style 201B as a makeup file to a printer device. In embodiments, the software application can further store the selected and/or adjusted cosmetic style 201B as a preset, such that the user can select and/or print the same cosmetic style 201B later.

As shown at FIG. 7D, the user 300 applies the selected and/or adjusted cosmetic style to a surface with the printer device 100. In embodiments, the surface is a face, skin, or hair. In embodiments, the user 300 is a second person, wherein a first person applies the cosmetic style to the second person. In embodiments, the first person can be a trained user, such as at a store, salon, spa, or makeup counter.

In operation, printer device 100 receives the makeup image file of the selected cosmetic style 201B from the smart device. The user 300 can hold the printer device 100 with the handle and move the printer over a surface. In embodiments, the surface is a face. In embodiments, the surface is skin or hair. In embodiments, the surface is a facial feature. As printer device 100 is moved over the surface, printer device 100 detects a position and a curvature of the body based on the position sensor and directs the printer to print the cosmetic style at a specific location, e.g., a location adjacent the printer applicator. In embodiments, the user 300 directs the printer device 100 over the surface before selecting, adjusting, and/or printing the cosmetic style. In such embodiments, printer device 100 is configured to detect a facial feature of the user 300 to enable the software application to provide a recommendation based on the user's facial features, detect a position of the one or more facial features, or a combination thereof.

In embodiments, the printer device 100 senses its own location at, on, or along the surface, and automatically applies one or more cosmetic style to the location on the surface. In embodiments, the cosmetic style is manually applied, as activated with a button or switch. In this manner, the printer device 100 prints the cosmetic style only in the location desired by the user, based on the cosmetic style selected, the adjustments made to the cosmetic style, or a combination thereof.

Figure 8:
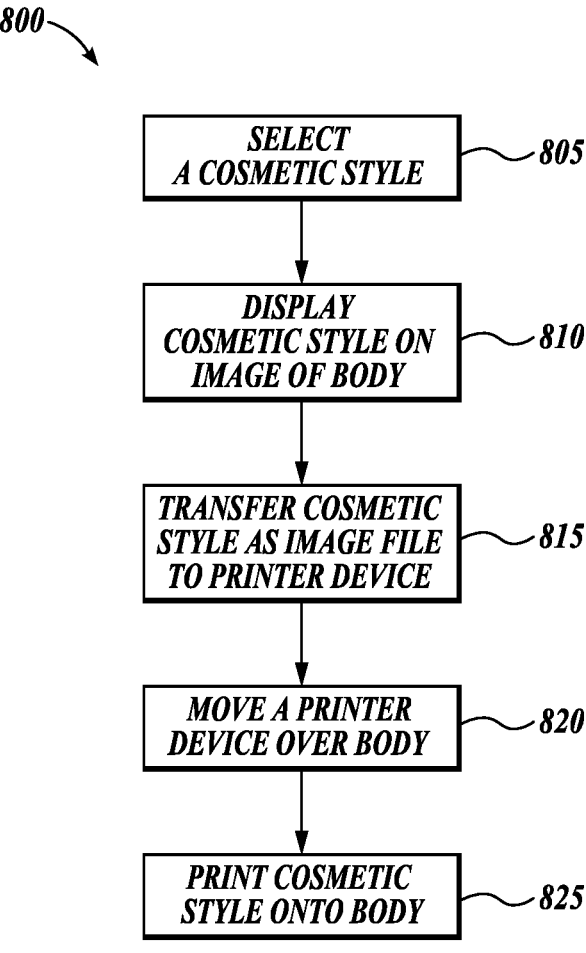
FIG. 8 shows an example first method of use of a system for selection and application of a cosmetic style.

In an aspect, a method of applying a cosmetic style with a system is provided. In embodiments, a method includes selecting the cosmetic style from a plurality of cosmetic styles, displaying the cosmetic style on an image of an individual, transferring the cosmetic style as an image file to a printer device, moving the printer device over a portion of the individual, and printing the cosmetic style onto the individual at a location based on one or more position sensors of the printer device. FIG. 8 shows an example method 800 of using an example system (e.g., system 2000 or system 2500), in accordance with the disclosure.

At block 805, a cosmetic style is selected. In embodiments, the cosmetic style is selected from a plurality of cosmetic styles. In embodiments, the cosmetic style is selected as shown at FIGS. 6A, 7A, or a combination thereof. In embodiments, the cosmetic style is selected from an eyebrow, an eyeshadow, a concealer, a primer, a foundation, a blush, a lipliner, a lipstick, a bronzer, an eyeliner, a freckle pattern, a facial hair, a hair design, a highlighter, or a combination thereof.

At block 810, the cosmetic style is displayed on an image of an individual. In embodiments, the image of the individual comprises a live video feed from a smart device or the printer device. In embodiments, the cosmetic style is displayed as shown at FIGS. 6B, 7B, or a combination thereof.

At block 815, the cosmetic style is stored as an image file and transferred to a printer device. In embodiments, the image file is a makeup image file. In embodiments, the image file is stored with a smart device software application. In embodiments, the printer device receives the image file of the cosmetic style through a wireless or wired connection with the smart device, such as shown at FIG. 2.

At block 820, the printer device is moved over the body of the individual. In embodiments, the printer device is moved as shown at FIG. 7D. In embodiments, the printer device is moved by an operator of the device onto a person. In embodiments, the printer device is moved by a user of the printer device, e.g., onto their own body.

At block 825, the cosmetic style is printed onto the body of the individual. In embodiments, the cosmetic style is printed at a location of the body as shown in the image of the body. In embodiments, the cosmetic style is printed by the printer device. In embodiments, the cosmetic style is comprised of one or more cosmetic dyes or inks stored inside one or more reservoirs of the printer device. In embodiments, a primer is applied before the cosmetic style is printed, and/or a topcoat is applied after the cosmetic style is printed.

Figure 9:
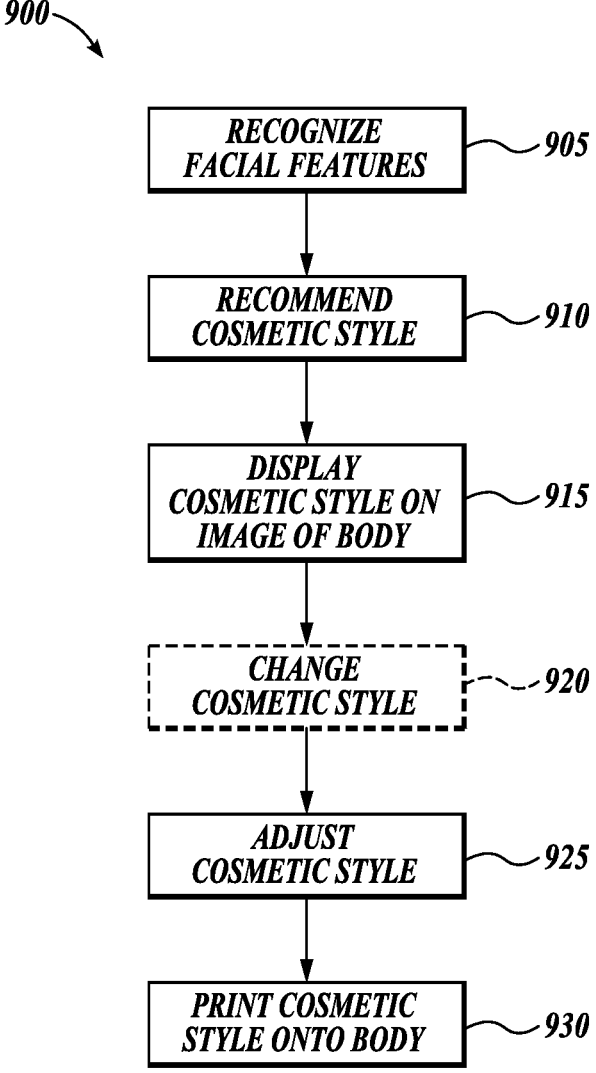
FIG. 9 shows an example second method of use of a system for selection and application of a cosmetic style.

FIG. 9 shows another example method 900 of using an example system of the disclosure.

At block 905, a plurality of facial features of the image of the body of the individual are recognized, e.g., by a software application of a smart device analyzing the image. In embodiments, the plurality of facial features is recognized by the printer device, through one or more cameras on the printer device. In embodiments, the depth and/or curvature of the plurality of facial features is recognized by the proximity sensor on the printer device. As described herein, facial features can include cheeks, cheekbones, eyes, eyelids, waterlines, lips, eyebrows, noses, hair lines, ears, chins, or the like.

At block 910, the system recommends a cosmetic style. In embodiments, the cosmetic style is recommended based on a trending cosmetic style, a color of a user's hair, skin, eyes, or lips, a past cosmetic style selected by the user, a shape of the user's eyes, eyebrows, nose, lips, cheeks, or forehead, a location of the user, or a color of the user's clothing. In embodiments, the cosmetic style is selected from an eyebrow, an eyeshadow, a concealer, a primer, a foundation, a blush, a lipliner, a lipstick, a bronzer, an eyeliner, a freckle pattern, a facial hair, a hair design, a highlighter, or a combination thereof.

At block 915, the cosmetic style is displayed on the image of the body of the individual, as described herein.

Optionally, at block 920, the user changes the selected cosmetic style. In embodiments, changing the cosmetic style includes selecting another cosmetic style from the plurality of cosmetic styles instead of the cosmetic style. In embodiments, the user can switch the cosmetic style multiple times before deciding to print the cosmetic style.

At block 925, the user adjusts the cosmetic style. In embodiments, adjusting the cosmetic style includes changing a color, a size, a length, a width, a hair size, a pattern, an angle, a position, a location of the cosmetic style, or a combination thereof of the cosmetic style.

At block 930, the system prints the cosmetic style onto a portion of the body of the individual. In embodiments, as described herein, the printer device accurately detects and prints the cosmetic style onto a specific location of a user's body.

It should be understood that method 800 and method 900 should be interpreted as merely representative and not exhaustive. In embodiments, process blocks of method 800 and 900 can be performed simultaneously, sequentially, in a different order, or even omitted, without departing from the scope of this disclosure.

Figure 10:
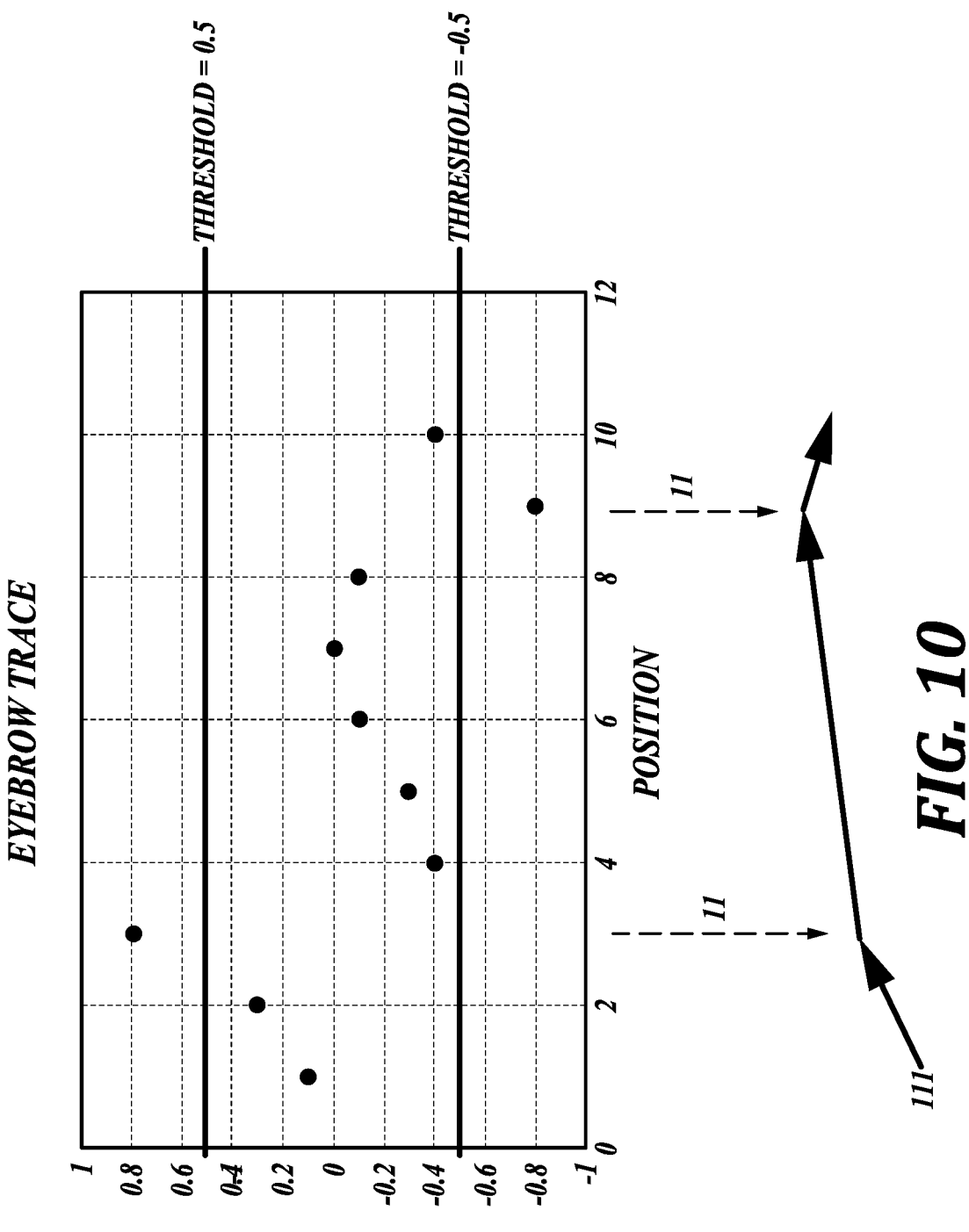
FIG. 10 shows an example graph of a second derivative of a curve fitted to a portion of skin of an individual, such as an eyebrow, with the second derivative plotted as a function of position along a length of the curve, as used for determining start and stop points for individual segments of a plurality of guide segments.

FIG. 10 shows an example graph of a second derivative of a curve fitted to a portion of skin of an individual, such as an eyebrow, with the second derivative plotted as a function of position along a length of the curve. The example graph, or a data structure encoding the data for the graph, can be used for determining start and stop points 11 for individual segments of the plurality of guide segments 111 as shown by the display. An example process, performable at least in part by a smart device and/or a printer device of the disclosure, for determining the plurality of guide segments, includes imaging the portion of the skin to produce an image of a feature of the portion of the skin (e.g., an image of an eyebrow), analyzing the feature of the portion of the skin to compute a geometrical curve that is fitted to the feature (e.g., a best-fit curve), computing a mathematical or polynomial representation of the curve, and computing a second derivative of the mathematical or polynomial representation of the curve (i.e., a rate of change of a curvature or slope of the curve; "slope of slope"). In embodiments, thresholds for the second derivative are used to determine whether a particular data point of the second derivative corresponds to a significant rate of change of curvature of the original mathematical or polynomial representation. For example, if thresholds of −0.5 and 0.5 are implemented, data of the second derivative that exceeds these thresholds indicates significant decreases and increases in the rate of change of the slope of the curve at a particular position along the curve. These points are used as start and stop points 11 for individual guide segments of the plurality of guide segments 111 as shown by the display.

Figure 11A:
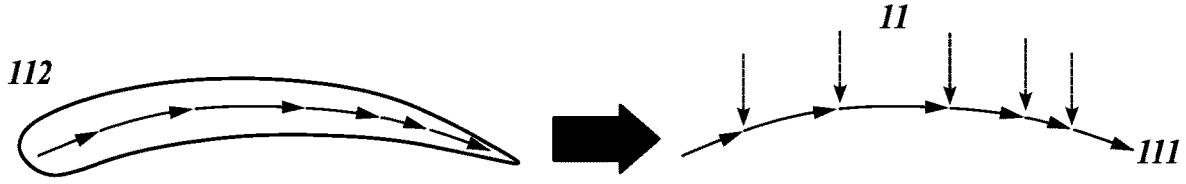
FIG. 11A shows a first eyebrow shape and a first curve fitted to the first eyebrow shape with a first plurality of guide segments.
Figure 11B:
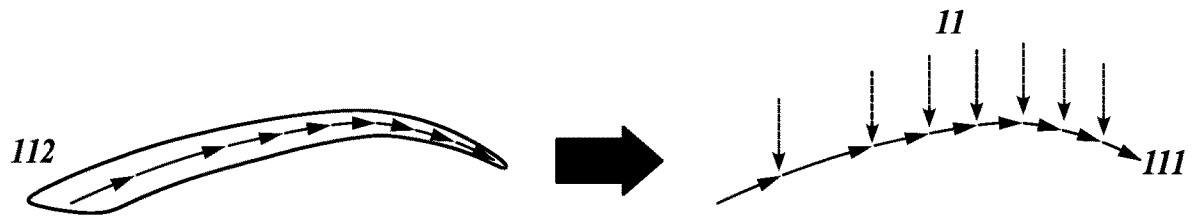
FIG. 11B shows a second eyebrow shape and a second curve fitted to the second eyebrow shape with a second plurality of guide segments.
Figure 11C:
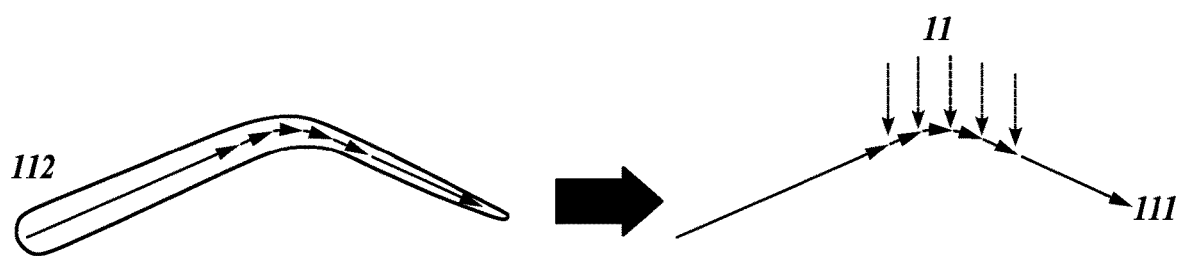
FIG. 11C shows a third eyebrow shape and a third curve fitted to the third eyebrow shape with a third plurality of guide segments.

In embodiments, such approaches are useful for producing guide segments for any feature shape or characteristic. For example, as shown at FIGS. 11A-11C, eyebrow shapes 112 are determined by image analysis of images of eyebrows and best-fit curves are computed and fitted to the eyebrow shapes 112. The curves are analyzed at the second derivative of the curves to determine start and stop points 11 for the plurality of guide segments 111 based on the rate of change of the slope of the original fitted curve at positions along the length of the curve. Eyebrows with gradual changes in slope, as shown at FIGS. 11A and 11B, have at least semi-regularly spaced start and stop points 11 along the plurality of guide segments 111, while eyebrows with sharper or more abrupt changes in slope, as shown at FIG. 11C, have corresponding groupings of start and stop points 11 at corresponding positions along the plurality of guide segments 111.

Figure 12A:
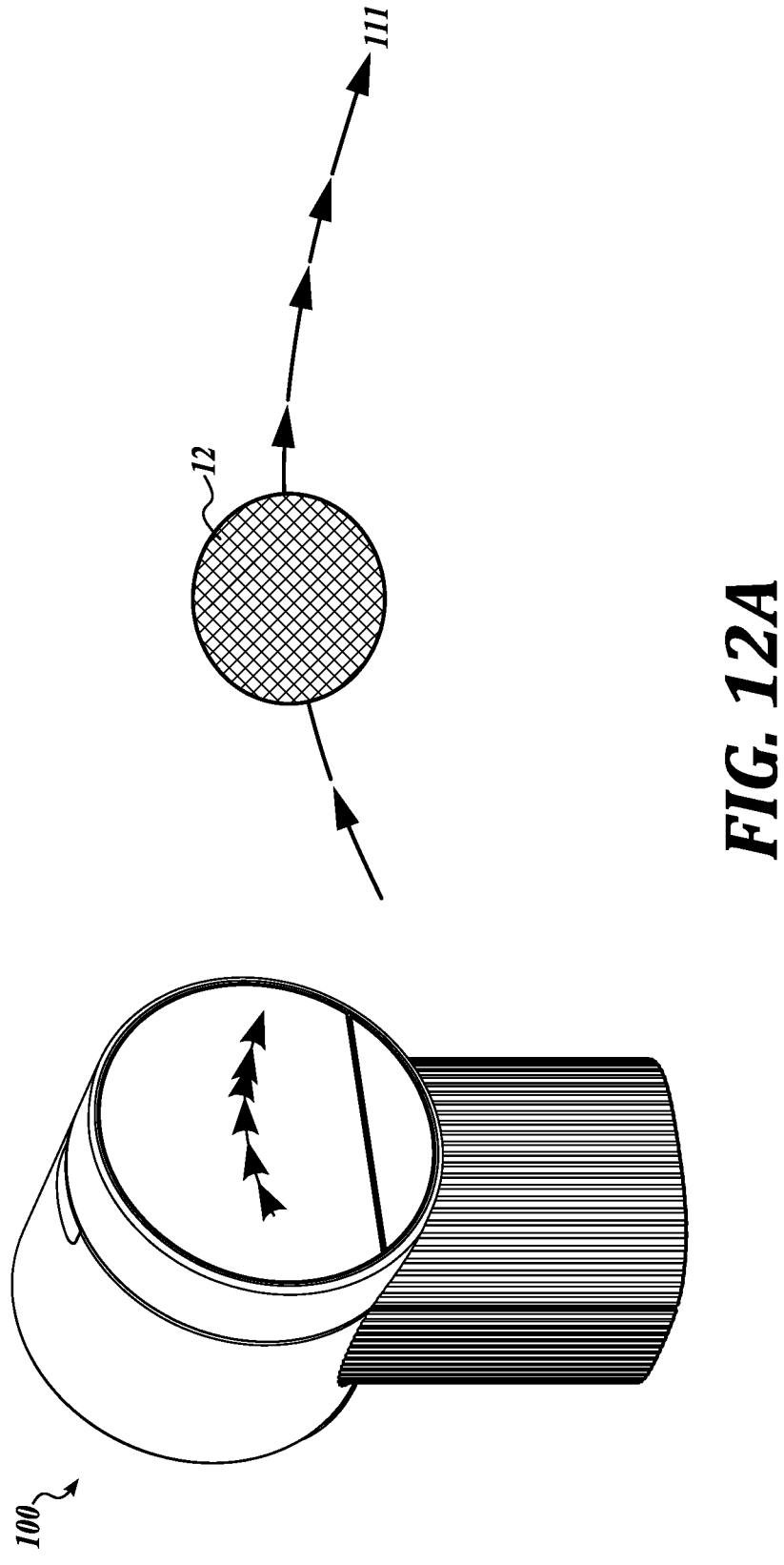
FIG. 12A shows a perspective view of an example printer device with a plurality of guide segments (left) and a correspondence between a printer applicator and the plurality of guide segments (right) during application of a cosmetic style, in an aligned position.

As shown at FIG. 12A, an example printer device 100 with a plurality of guide segments depicted on a display (left) is shown next to a conceptual representation of a printer applicator 12 as it relates to the plurality of guide segments 111 (right) during application of a cosmetic style.

Figure 12B:
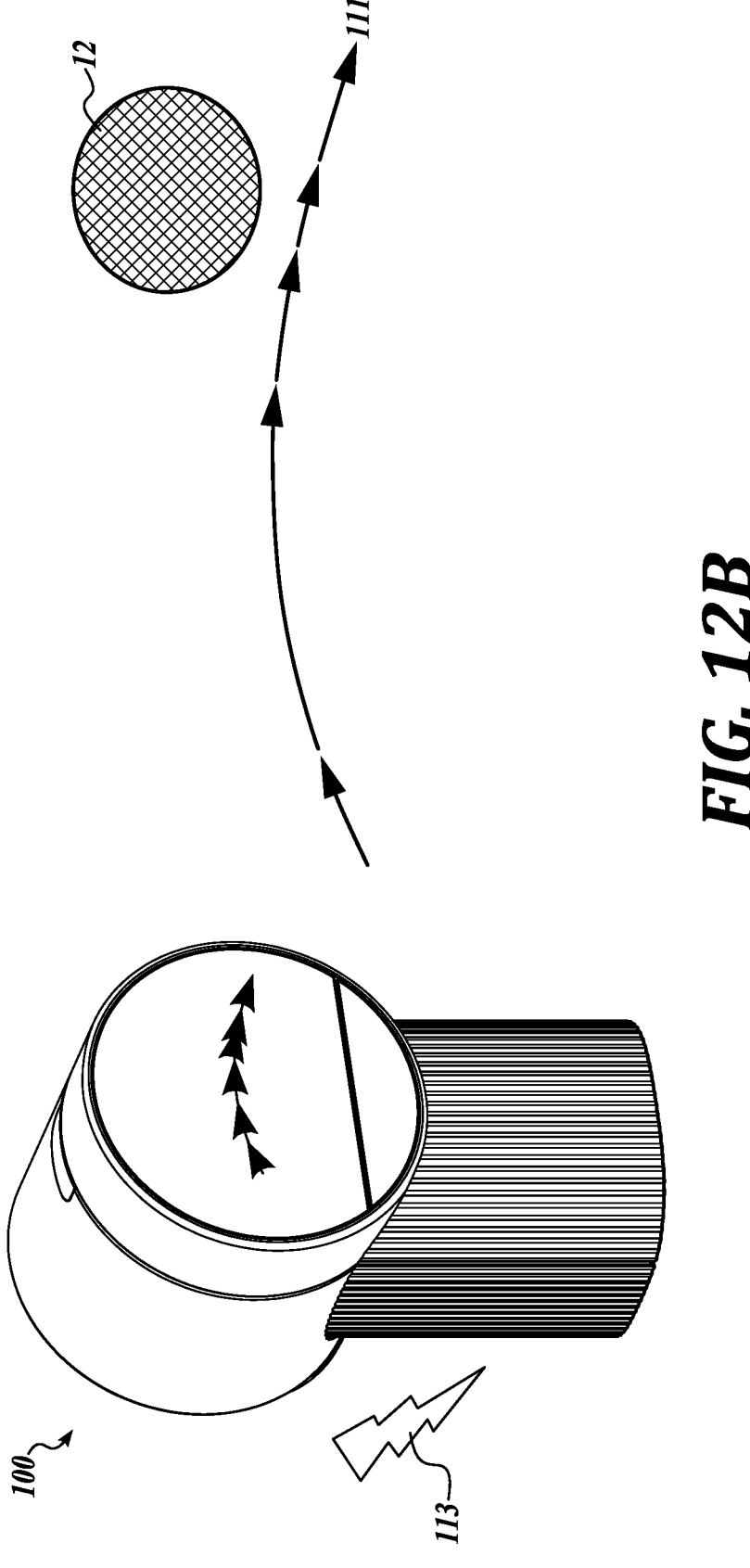
FIG. 12B shows a perspective view of the example printer device with the plurality of guide segments (left) and a correspondence between the printer applicator and the plurality of guide segments (right) during application of the cosmetic style, in a non-aligned position.

In the shown configuration, the printer applicator 12 is adjacent to a portion of skin intended to be printed and is in an aligned position with the plurality of guide segments 111. As the printer device 100 is moved along the length of the feature of the skin and printing ensues, the printer device 100 may be misaligned with the skin intended to be printed. In such cases, as shown at FIG. 12B, the printer applicator 12 is in a non-aligned position and a feedback device or component generates a feedback 113 for the individual to alert the individual of the need to change the course of the printer device 100. In embodiments, practice methods of "dry runs" of the printer device 100 can be used for the individual to practice the motion of applying the cosmetic style to the portion of the skin without actually applying the cosmetic style to the skin. In this manner, the individual is better prepared to actually apply the cosmetic style to the skin and has a lower risk of error and resultant feedback 113. In embodiments, the feedback 113 provided to the user by the feedback device or component comprises audio feedback, visual feedback, audiovisual feedback, or haptic feedback.

Figure 13:
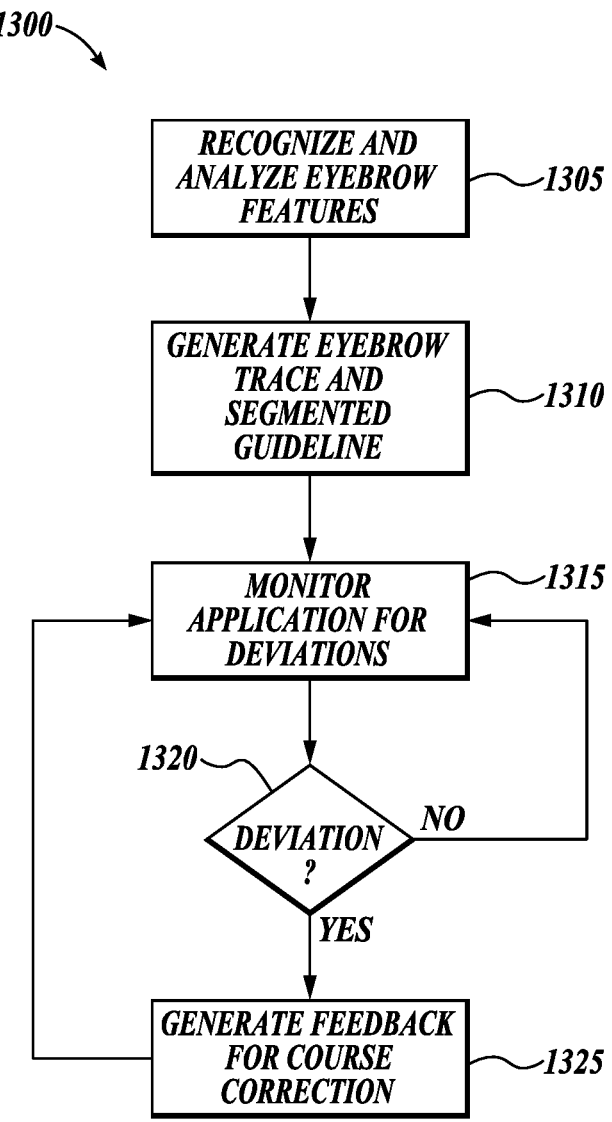
FIG. 13 shows an example method for monitoring the application of a cosmetic style by a device and/or system of the disclosure and generating feedback for an individual to correct the application of the cosmetic style in real time.

As shown at FIG. 13, an example method 1300 for monitoring application of a cosmetic style by a device and/or system of the disclosure and generating feedback for an individual to correct the application of the cosmetic style in real time is shown.

At block 1305, the printer device or system recognizes and analyzes eyebrow features. In embodiments, this occurs as a result of image analysis of an image of an eyebrow of the face of the individual.

At block 1310, the printer device or system generates an eyebrow trace and/or best-fit curve and computes and generates the segmented guideline. In embodiments, computation of the plurality of segmented guidelines occurs by computing the second derivative of the mathematical or polynomial representation of the curve, and comparing data points of the second derivative against one or more thresholds, as described herein.

At block 1315, during application of the cosmetic style to the skin, the printer device or system monitors the application of the cosmetic style for deviations from the intended trajectory of application. In embodiments, this monitoring occurs continuously during the application of the cosmetic style, for example, as part of a repeated logical loop.

At block 1320, if a deviation from the intended trajectory is detected (block 1320: YES), the printer device or system generates feedback for the user to correct the application, and if no deviation from the intended trajectory is detected (block 1320: NO), the printer device or system continues to monitor the application for deviations at step 1315. Block 1320 can be considered as a subset of step 1315 and corresponds to a logical determination of whether the deviation occurs.

The present disclosure may reference quantities and numbers. Unless specifically stated, such quantities and numbers are not to be considered restrictive, but representative of the possible quantities or numbers associated with the present disclosure. Also, in this regard, the present disclosure may use the term "plurality" to reference a quantity or number. In this regard, the term "plurality" is meant to be any number that is more than one, for example, two, three, four, five, etc. The terms "about," "approximately," "near." etc., mean plus or minus 5% of the stated value. For the purposes of the present disclosure, the phrase "at least one of A, B, and C." for example, means (A), (B), (C), (A and B), (A and C), (B and C), or (A, B, and C), including all further possible permutations when greater than three elements are listed.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices or components such as a processor (e.g., a microprocessor), a central processing unit (CPU), a digital signal processor (DSP), an application-specific integrated circuit (ASIC), a field-programmable gate array (FPGA), or the like, or any combination thereof, and can include discrete digital or analog circuit elements or electronics, or combinations thereof.

An embodiment includes one or more data stores that, for example, stores instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes a computer-readable media drive or memory slot configured to accept signal-bearing medium (e.g., computer-readable memory media, computer-readable recording media, or the like). In an embodiment, a program for causing a device and/or system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of example embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present disclosure may include references to directions, such as "vertical," "horizontal," "front," "rear." "left," "right." "top." and "bottom," etc. These references, and other similar references in the present application, are intended to assist in helping describe and understand the particular embodiment (such as when the embodiment is positioned for use) and are not intended to limit the present disclosure to these directions or locations.

The principles, example embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

NON-LIMITING EMBODIMENTS

While general features of the disclosure are described and shown and particular features of the disclosure are set forth in the claims, the following non-limiting embodiments relate to features, and combinations of features, that are explicitly envisioned as being part of the disclosure. The following non-limiting Embodiments contain elements that are modular and can be combined with each other in any number, order, or combination to form a new non-limiting Embodiment, which can itself be further combined with other non-limiting Embodiments.

Embodiment 1. A printer device for application of a cosmetic style to a portion of a skin of an individual, the printer device comprising: a printer comprising a printer applicator operably connected to a reservoir comprising a dye therein; a position sensor configured to detect a position of the printer applicator relative to the portion of the skin; a display configured to represent the portion of the skin as a plurality of guide segments, and represent the position of the printer applicator as a visual indicator relative to the plurality of guide segments; wherein a position of the visual indicator as depicted by the display responds to a change in the position of the printer applicator relative to the portion of the skin; and circuitry operably connected to the printer, the position sensor, and the display, wherein the circuitry is configured to: direct the printer to print the cosmetic style with passage of the dye from the reservoir through the printer applicator to the portion of the skin; compute the position of the printer applicator relative to the portion of the skin based on the position sensor; compute a depiction of the visual indicator relative to a guide segment of the plurality of guide segments based on the position of the printer applicator relative to the portion of the skin; and transmit to the display for the depiction of the visual indicator relative to the plurality of guide segments by the display.

Embodiment 2. The printer device of any other Embodiment, wherein the position sensor comprises a camera configured to capture a plurality of images, wherein the position of the printer applicator relative to the portion of the skin is computed by the circuitry of the printer device of claim 1 based at least in part on an image produced by the camera.

Embodiment 3. The printer device of any other Embodiment, wherein the position sensor comprises a rolling position sensor configured to contact at or near the portion of the skin as the rolling position sensor rolls over the skin and to measure a curvature of the skin.

Embodiment 4. The printer device of any other Embodiment, wherein the circuitry is further configured to: detect a deviation of the position of the printer applicator from the portion of the skin; and direct a feedback device to provide feedback to a user based on the detected deviation of the position of the printer applicator from the portion of the skin.

Embodiment 5. The printer device of any other Embodiment, wherein the circuitry is further configured to: detect a deviation of the visual indicator from the guide segment of the plurality of guide segments; and direct a feedback device to provide feedback to a user based on the detected deviation of the visual indicator from the guide segment of the plurality of guide segments.

Embodiment 6. The printer device of any other Embodiment, wherein the feedback device is a component of the printer device, and wherein the feedback provided to the user by the feedback device comprises audio feedback, visual feedback, audiovisual feedback, or haptic feedback.

Embodiment 7. The printer device of any other Embodiment, wherein the feedback provided by the feedback device comprises haptic feedback.

Embodiment 8. The printer device of any other Embodiment, wherein the circuitry is further configured to: compute a trace of the portion of the skin of the individual based on an image of the portion of the skin; compute a curvature of the trace of the portion of the skin; and compute a number and configuration of the plurality of guide segments based on the curvature of the trace of the portion of the skin.

Embodiment 9. The printer device of any other Embodiment, wherein the portion of the skin comprises a facial feature for receipt of the cosmetic style thereon.

Embodiment 10. The printer device of any other Embodiment, wherein the facial feature comprises an eyebrow.

Embodiment 11. The printer device of any other Embodiment, wherein the printer applicator is positioned at a first side of the printer device and the display is positioned at a second side of the printer device, wherein the first side is positioned opposite the second side on the printer device.

Embodiment 12. The printer device of any other Embodiment, wherein the plurality of guide segments is depicted by the display as being at least approximately superimposable with the portion of the skin, such that during use of the printer device, the plurality of guide segments visually corresponds to the portion of the skin.

Embodiment 13. A system for application of a cosmetic style to a portion of a skin of an individual, the system comprising: the printer device of any other Embodiment; and a smart device comprising circuitry configured to: select the cosmetic style from a plurality of cosmetic styles;

display the cosmetic style on an image of the portion of the skin of the individual; and transmit the cosmetic style as a makeup image file to the printer device; wherein the circuitry of the printer device of any other Embodiment is operably connected to the circuitry of the smart device and is further configured to: receive the makeup image file from the smart device; and direct the printer to print the cosmetic style with passage of the dye from the reservoir through the printer applicator to the portion of the skin based on the makeup image file.

Embodiment 14. The system of any other Embodiment, wherein the circuitry of the smart device comprises a processor and a non-transitory machine-readable medium storing processor-executable instructions which when executed by the processor configure the processor to select the cosmetic style from the plurality of cosmetic styles, display the cosmetic style on the image of the portion of the skin of the individual, and transmit the cosmetic style as the makeup image file to the printer device.

Embodiment 15. The system of any other Embodiment, wherein the circuitry of the printer device comprises a processor and a non-transitory machine-readable medium storing processor-executable instructions which when executed by the processor configure the processor to receive the makeup image file from the smart device, and direct the printer to print the cosmetic style with passage of the dye from the reservoir through the printer applicator to the portion of the skin based on the makeup image file.

Embodiment 16. A method of applying a cosmetic style with the printer device of any other Embodiment, the method comprising: moving the printer device over the portion of the skin of the individual; printing the cosmetic style onto the portion of the skin at a location adjacent to the printer applicator; and guiding movement of the printer device over the portion of the skin based on: the depiction of the visual indicator relative to the plurality of guide segments by the display, and optionally, feedback provided from a feedback device based on a detected deviation of the visual indicator from the guide segment of the plurality of guide segments.

Embodiment 17. The method of any other Embodiment, wherein the feedback device is a component of the printer device, and wherein the feedback provided to the user by the feedback device comprises audio feedback, visual feedback, audiovisual feedback, or haptic feedback.

Embodiment 18. The method of any other Embodiment, wherein the feedback provided by the feedback device comprises haptic feedback.

Embodiment 19. The method of any other Embodiment, wherein the portion of the skin comprises a facial feature for receipt of the cosmetic style thereon.

Embodiment 20. The method of any other Embodiment, wherein the facial feature comprises an eyebrow.

While illustrative embodiments have been illustrated and described, it will be appreciated that various changes can be made therein without departing from the spirit and scope of the invention.

The embodiments of the invention in which an exclusive property or privilege is claimed are defined as follows:

1. A printer device for application of a cosmetic style to a portion of a skin of an individual, the printer device comprising:
   a printer comprising a printer applicator operably connected to a reservoir comprising a dye therein;
   a position sensor configured to detect a position of the printer applicator relative to the portion of the skin;

a display configured to represent the portion of the skin as a plurality of guide segments, and represent the position of the printer applicator as a visual indicator relative to the plurality of guide segments; wherein a position of the visual indicator as depicted by the display responds to a change in the position of the printer applicator relative to the portion of the skin;
   circuitry operably connected to the printer, the position sensor, and the display, wherein the circuitry is configured to:
      compute the position of the printer applicator relative to the portion of the skin based on the position sensor;
      compute a depiction of the visual indicator relative to a guide segment of the plurality of guide segments based on the position of the printer applicator relative to the portion of the skin; and
      transmit to the display for the depiction of the visual indicator relative to the plurality of guide segments by the display; and
   a smart device comprising circuitry configured to:
      select the cosmetic style from a plurality of cosmetic styles;
      display the cosmetic style on an image of the portion of the skin of the individual; and
      transmit the cosmetic style as a makeup image file to the printer device,
   wherein the circuitry of the printer device is operably connected to the circuitry of the smart device and is further configured to:
      receive the makeup image file from the smart device; and
      direct the printer to print the cosmetic style with passage of the dye from the reservoir through the printer applicator to the portion of the skin based on the makeup image file.

2. The printer device of claim 1, wherein the position sensor comprises a camera configured to capture a plurality of images, wherein the position of the printer applicator relative to the portion of the skin is computed by the circuitry of the printer device of claim 1 based at least in part on an image produced by the camera.

3. The printer device of claim 1, wherein the position sensor comprises a rolling position sensor configured to contact at or near the portion of the skin as the rolling position sensor rolls over the skin and to measure a curvature of the skin.

4. The printer device of claim 1, wherein the circuitry is further configured to:
   detect a deviation of the position of the printer applicator from the portion of the skin; and
   direct a feedback device to provide feedback to a user based on the detected deviation of the position of the printer applicator from the portion of the skin.

5. The printer device of claim 1, wherein the circuitry is further configured to:
   detect a deviation of the visual indicator from the guide segment of the plurality of guide segments; and
   direct a feedback device to provide feedback to a user based on the detected deviation of the visual indicator from the guide segment of the plurality of guide segments.

6. The printer device of claim 5, wherein the feedback device is a component of the printer device, and wherein the feedback provided to the user by the feedback device comprises audio feedback, visual feedback, audiovisual feedback, or haptic feedback.

7. The printer device of claim 6, wherein the feedback provided by the feedback device comprises haptic feedback.

8. The printer device of claim 1, wherein the circuitry is further configured to:

compute a trace of the portion of the skin of the individual based on an image of the portion of the skin;

compute a curvature of the trace of the portion of the skin; and compute a number and configuration of the plurality of guide segments based on the curvature of the trace of the portion of the skin.

9. The printer device of claim 8, wherein the portion of the skin comprises a facial feature for receipt of the cosmetic style thereon.

10. The printer device of claim 9, wherein the facial feature comprises an eyebrow.

11. The printer device of claim 1, wherein the printer applicator is positioned at a first side of the printer device and the display is positioned at a second side of the printer device, wherein the first side is positioned opposite the second side on the printer device.

12. The printer device of claim 11, wherein the plurality of guide segments is depicted by the display as being at least approximately superimposable with the portion of the skin, such that during use of the printer device, the plurality of guide segments visually corresponds to the portion of the skin.

13. A system for application of a cosmetic style to a portion of a skin of an individual, the system comprising:

a printer device comprising:

a printer comprising a printer applicator operably connected to a reservoir comprising a dye therein:

a position sensor configured to detect a position of the printer applicator relative to the portion of the skin;

a display configured to represent the portion of the skin as a plurality of guide segments, and represent the position of the printer applicator as a visual indicator relative to the plurality of guide segments:

wherein a position of the visual indicator as depicted by the display responds to a change in the position of the printer applicator relative to the portion of the skin; and a smart device comprising circuitry configured to: select the cosmetic style from a plurality of cosmetic styles;

display the cosmetic style on an image of the portion of the skin of the individual; and transmit the cosmetic style as a makeup image file to the printer device, wherein circuitry of the printer device is operably connected to the circuitry of the smart device and is further configured to: receive the makeup image file from the smart device; and direct the printer to print the cosmetic style with passage of the dye from the reservoir through the printer applicator to the portion of the skin based on the makeup image file.

14. The system of claim 13, wherein the circuitry of the smart device comprises a processor and a non-transitory machine-readable medium storing processor-executable instructions which when executed by the processor configure the processor to select the cosmetic style from the plurality of cosmetic styles, display the cosmetic style on the image of the portion of the skin of the individual, and transmit the cosmetic style as the makeup image file to the printer device.

15. The system of claim 13, wherein the circuitry of the printer device comprises a processor and a non-transitory machine-readable medium storing processor-executable instructions which when executed by the processor configure the processor to receive the makeup image file from the smart device, and direct the printer to print the cosmetic style with passage of the dye from the reservoir through the printer applicator to the portion of the skin based on the makeup image file.

16. A method of applying a cosmetic style with a printer device comprising:

a printer comprising a printer applicator operably connected to a reservoir comprising a dye therein;

a position sensor configured to detect a position of the printer applicator relative to the portion of the skin;

a display configured to represent the portion of the skin as a plurality of guide segments, and represent the position of the printer applicator as a visual indicator relative to the plurality of guide segments; wherein a position of the visual indicator as depicted by the display responds to a change in the position of the printer applicator relative to the portion of the skin; and a smart device comprising circuitry configured to:

select the cosmetic style from a plurality of cosmetic styles;

display the cosmetic style on an image of the portion of the skin of the individual; and transmit the cosmetic style as a makeup image file to the printer device, wherein circuitry of the printer device is operably connected to the circuitry of the smart device and is further configured to:

receive the makeup image file from the smart device; and direct the printer to print the cosmetic style with passage of the dye from the reservoir through the printer applicator to the portion of the skin based on the makeup image file, the method comprising:

moving the printer device over the portion of the skin of the individual;

printing the cosmetic style onto the portion of the skin at a location adjacent to the printer applicator; and guiding movement of the printer device over the portion of the skin based on:

the depiction of the visual indicator relative to the plurality of guide segments by the display, and optionally, feedback provided from a feedback device based on a detected deviation of the visual indicator from the guide segment of the plurality of guide segments.

17. The method of claim 16, wherein the feedback device is a component of the printer device, and wherein the feedback provided to the user by the feedback device comprises audio feedback, visual feedback, audiovisual feedback, or haptic feedback.

18. The method of claim 17, wherein the feedback provided by the feedback device comprises haptic feedback.

19. The method of claim 16, wherein the portion of the skin comprises a facial feature for receipt of the cosmetic style thereon.

20. The method of claim 19, wherein the facial feature comprises an eyebrow.

21. The system of claim 13, wherein the circuitry of the printer device is configured to:

compute the position of the printer applicator relative to the portion of the skin based on the position sensor;

compute a depiction of the visual indicator relative to a guide segment of the plurality of guide segments based on the position of the printer applicator relative to the portion of the skin; and transmit to the display for the depiction of the visual indicator relative to the plurality of guide segments by the display.

\* \* \* \* \*